United States Patent [19]

Trulson et al.

[11] Patent Number: 6,143,562
[45] Date of Patent: Nov. 7, 2000

[54] CARBON-BASED PROCESS FOR SELECTION OF TRANSGENIC PLANT CELLS

[75] Inventors: Anna Julia Trulson; Charles Edward Green, both of Davis; Carl Joseph Braun, III, Woodland, all of Calif.

[73] Assignee: Seminis Vegetable Seeds, Saticoy, Calif.

[21] Appl. No.: 09/076,359

[22] Filed: May 12, 1998

Related U.S. Application Data

[63] Continuation of application No. 08/417,618, Apr. 6, 1995, abandoned.

[51] Int. Cl.$^7$ ............................ C12N 15/29; C12N 15/82; A01H 4/00; A01H 5/00
[52] U.S. Cl. ........................ 435/420; 435/419; 435/468; 435/320.1; 536/23.6; 536/24.1; 800/295; 800/298
[58] Field of Search ........................ 435/420, 419, 435/468, 320.1; 536/23.6, 24.1; 800/295, 298

[56] References Cited

U.S. PATENT DOCUMENTS

| | | |
|---|---|---|
| 3,514,900 | 6/1970 | McDade . |
| 4,038,778 | 8/1977 | Kadkade . |
| 4,473,648 | 9/1984 | Tang . |
| 4,634,674 | 1/1987 | Shahin . |
| 4,665,030 | 5/1987 | Close . |
| 4,665,031 | 5/1987 | Péron . |
| 4,717,664 | 1/1988 | Hara et al. . |
| 4,830,966 | 5/1989 | Close . |
| 4,851,346 | 7/1989 | Chan . |
| 4,943,674 | 7/1990 | Houck et al. ........................ 800/205 |
| 5,034,322 | 7/1991 | Rogers et al. . |
| 5,041,382 | 8/1991 | Gupta et al. . |
| 5,066,595 | 11/1991 | Hubbard et al. . |
| 5,188,958 | 2/1993 | Moloney et al. . |
| 5,236,841 | 8/1993 | Gupta et al. . |
| 5,238,841 | 8/1993 | Kinnersley et al. . |
| 5,294,549 | 3/1994 | Pullman et al. . |
| 5,302,523 | 4/1994 | Coffee et al. . |
| 5,350,689 | 9/1994 | Shillito et al. . |
| 5,365,016 | 11/1994 | Burrell et al. . |
| 5,387,756 | 2/1995 | Burrell et al. . |

FOREIGN PATENT DOCUMENTS

| | | |
|---|---|---|
| 0 368 506 A2 | 5/1990 | European Pat. Off. . |
| 0 438 904 A1 | 7/1991 | European Pat. Off. . |
| 0 455 316 A2 | 11/1991 | European Pat. Off. . |
| 0 466 995 A2 | 1/1992 | European Pat. Off. . |
| 0 485 044 A2 | 5/1992 | European Pat. Off. . |
| 0 521 621 A2 | 1/1993 | European Pat. Off. . |
| 0 530 978 A2 | 3/1993 | European Pat. Off. . |
| 0 470 145 B1 | 4/1994 | European Pat. Off. . |
| WO 92/11375 | 7/1992 | WIPO . |
| WO 92/11376 | 7/1992 | WIPO . |
| WO 92/11382 | 7/1992 | WIPO . |
| WO 92/14831 | 9/1992 | WIPO . |
| WO 94/04693 | 3/1994 | WIPO . |
| WO 94/09144 | 4/1994 | WIPO . |
| WO 94/11520 | 5/1994 | WIPO . |
| WO 94/20627 | 9/1994 | WIPO . |

OTHER PUBLICATIONS

Chilton et al., "Agrobacterium tumefaciens DNA and PS8 Bacteriophage DNA Not Detected in Crown Gall Tumors," *Proc. Nat. Acad. Sci. USA*, vol. 71, No. 9, 1974, pp. 3672–3676.

Fennell et al., "Electroporation and PEG delivery of DNA into maize microspores," *Plant Cell Reports*, vol. 11, 1992, pp. 567–570.

Goldberg, "Plants: Novel Developmental Processes," *Science*, vol. 240, 1988, pp. 1460–1467.

Leemans, "Ti to Tomato, Tomato to Market, A decade of plant biotechnology," *Bio/Technology*, vol. 11, 1993, pp. S22–S26.

Murashige et al., "A Revised Medium for Rapid Growth and Bio Assays with Tobacco Tissue Cultures," *Physiologia Plantarum*, vol. 15, 1962, pp. 473–497.

Perl et al., "Bacterial Dihydrodipicolinate Synthase and Desensitized Aspartate Kinase: Two Novel Selectable Markers for Plant Transformation," *Bio/Technology*, vol. 11, 1993, pp. 715–718.

Shaw et al., "The Structure and Physiological Activity of Some N6–Substituted Adenines," *Phytochemistry*, vol. 10, 1971, pp. 2329–2336.

Sheehy et al., "Reduction of polygalacturonase activity in tomato fruit by antisense RNA," *Proc. Natl. Acad. Sci. USA*, vol. 85, 1988, 8805–8809.

Smith et al. "PMI40, an Intron–Containing Gene Required for Early Steps in Yeast Mannosylation," *Molecular and Cellular Biology*, vol. 12, No. 7, 1992, pp. 2924–2930.

Stark et al. "Regualtion of the Amount of Starch in Plant Tissues by ADP Glucose Pyrophosphorylase," *Science*, vol. 258, 1992, pp. 287–292.

(List continued on next page.)

*Primary Examiner*—Douglas W. Robinson
*Assistant Examiner*—Thomas Haas
*Attorney, Agent, or Firm*—Rockey, Milnamow & Katz, Ltd.

[57] ABSTRACT

A carbon-based process for the selection of heterotrophically cultured plant cells is contemplated as are plants transformed using that process and a kit useful for effecting such a transformation. Plant cells are transformed with a heterologous DNA segment that contains two expression cassettes. The first cassette contains a gene that encodes a heterologous enzyme that on expression converts a growth-limiting (encrypted) carbon source that does not support growth and proliferation of non-transformed plant cells into a carbon source that supports growth and proliferation of transformed plant cells. The second cassette contains a second gene to be expressed in the transformed plant cells. A mixture transformed and non-transformed plant cells is cultured under heterotrophic culture conditions with the growth-limiting carbon source as the only carbon source. Inasmuch as only the transformed cells express the heterologous enzyme that converts the carbon source present into a carbon source that is useful to support growth and proliferation, only transformed cells grow and proliferate, and those cells are selected.

19 Claims, 3 Drawing Sheets

OTHER PUBLICATIONS

Stoop et al. "Mannitol Metabolism in Celery Stressed by Excess Macronutrients," *Plant Physiol.,* vol. 106, 1994, pp. 503–511.

Thomas et al. "Metabolite Signals Regulate Gene Expression and Source/Sink Relations in Cereal Seedlings," *Plant Physiol.* vol. 106, 1994, pp. 1235–1239.

Voelker et al. "Fatty Acid Biosynthesis Redirected to Medium Chains in Trasgenic Oilseed Plants," *Science,* vol. 257, 1992, pp. 72–74.

Smith et al., "PM140, an Intron–Containing Gene Required for Early Steps in Yeast Mannosylation", *Molecular and Cellular Biology,* vol. 12, No. 7, Jul. 1992, pp. 2924–2930.

Collins et al., "Sequence of the phosphomannose isomerase–encoding gene of *Salmonella typhimurium,*" *Gene,* vol. 103, 1991, pp. 135–136.

Miles et al., "Nucleotide sequence and transcriptional start point of the phosphomannose isomerase gene (man A) of *Escherichia coli,*" *Gene,* vol. 32, 1984, pp. 41–48.

Darzins et al., "Nucleotide sequence analysis of the phosphomannose isomerase gene (pmi) of *Pseudomonas aeruginosa* and comparison with the corresponding *Escherichia coli* gene man A," *Gene,* vol. 42, 1986, pp. 293–302.

Schmidt et al., "The Rhizobium meliloti pmi gene encodes a new type of phosphomannose isomerase", *Gene,* vol. 122, 1992, pp. 35–43.

Graham et al., "Carbon Catabolite Repression Regulates Glyoxylate Cycle Gene Expression in Cucumber", *The Plant Cell,* vol. 6, May 1994, pp. 761–772.

Li et al., "A Sulfonylurea Herbicide Resistance Gene from *Arabidopsis thaliana* as a New Selectable Marker for Production of Fertile Transgenic Rice Plants," *Plant Physiol.,* vol. 100, 1992, pp. 662–668.

Perez et al., "Phleomycin resistance as a dominant selectable marker for plant cell transformation", *Plant Molecular Biology,* vol. 13, 1989, pp. 365–373.

Perl et al., "Bacterial Dihydrodipicolinate Synthase and Desensitized Aspartate Kinase: Two Novel Selectable Markers for Plant Transformation", *Bio/Technology,* vol. 11, Jun. 1993, pp. 715–718.

Shaul et al., "Increased lysine synthesis in tobacco plants that express high levels of bacterial dihydrodipicolinate synthase in their chloroplasts", *The Plant Journal,* vol. 2(2), 1992, pp. 203–209.

Tamura et al., "Blasticidin S Deaminase GEne (BSD): a New Selection Marker Gene for Transformation of *Arabidopsis thaliana* and *Nicotiana tabacum*", *Biosci. Biotech. Biochem.,* vol. 59(12), 1995, pp. 2336–2338.

Hayford et al., "Development of a Plant Transformation Selection System Based on Expression of Genes Encoding Gentamicin Acetyltransferases", *Plant Physiol.,* vol. 86, 1987, pp. 1216–1222.

Herrera–Estrella et al., "Chimeric genes as dominant selectable markers in plant cells," *The EMBO Journal,* vol. 2, No. 6, 1983, pp. 987–995.

Dennehey et al., "Comparison of selective agents for use with the selectable marker gene bar in maize transformation", *Plant Cell, Tissue and Organ Culture,* vol. 36, 1994, pp. 1–7.

Guerineau et al., "Sulfonamide resistance gene for plant transformation", *Plant Molecular Biology,* vol. 15, 1990, pp. 127–136.

Torbert et al., "Use of paromomycin as a selective agent for oat transformation", *Plant Cell Reports,* vol. 14, 1995, pp. 635–640.

Gossele et al., "A 6' gentamicin acetyltransferase gene allows effective selection of tobacco transformants using kanamycin as a substrate", *Plant Molecular Biology,* vol. 26, 1994, pp. 2009–2012.

Schaff, "The adenine phosphoribosyltransferase (APRT) selectable marker system", *Plant Science,* vol. 101, 1994, pp. 3–9.

Schroder et al., "Transformation of *Brassica napus* by using the aadA gene as selectable marker and inheritance studies of the marker genes", *Physiologia Plantarum,* vol. 92, 1994, pp. 37–46.

Waldron et al., "Resistance to hygromycin B", *Plant Molecular Biology,* vol. 5, 1985, pp. 103–108.

Akama et al, "Efficient Agrobacterium–mediated transformation of *Arabidopsis thaliana* using the bar gene as selectable marker", *Plant Cell Reports,* vol. 14, 1995, pp. 450–454.

Windhovel et al., "Expression of *Erwinia uredovora* Phytoene Desaturase in Synechococcus PCC7942 Leading to Resistance against a Bleaching Herbicide", *Plant Physiol.,* vol. 104, 1994, pp. 119–125.

van den Elzen et al., "A chimaeric hygromycin resistance gene as a selectable marker in plant cells", *Plant Molecular Biology,* vol. 5, 1985, pp. 299–302.

Hauptmann et al., "Evaluation of Selectable Markers for Obtaining Stable Transformants in the Gramineae", *Plant Physiol.,* vol. 86, 1988, pp. 602–606.

Bevan et al., "A chimaeric antibiotic resistance gene as a selectable marker for plant cell transformation", *Nature,* vol. 304, 1983, pp. 184–187.

Dekeyser et al., "Evaluation of Selectable Markers for Rice Transformation", *Plant Physiol.,* vol. 90, 1989, pp. 217–223.

Stalker et al., "Herbicide Resistance in Transgenic Plants Expressing a Bacterial Detoxification Gene," *Science,* vol. 242, 1988, pp. 419–423.

Shah et al., "Engineering Herbicide Tolerance in Transgenic Plants," *Science,* vol. 233, 1986, pp. 478–481.

White et al., "A cassette containing the bar gene of *Streptomyces hygroscopicus:* a selectable marker for plant transformation", *Nucleic Acids Research,* vol. 18, No. 4, 1989, p. 1062.

Streber et al., "Transgenic Tobacco Plants Expressing A Bacterial Detoxifying Enzyme are Resistant to 2,4–D," *Bio/Technology,* pp. 811–816.

Block et al., "Engineering herbicide resistance in plants by expression of a detoxifying enzyme", *The EMBO Journal,* vol. 6, No. 9, 1987, pp. 2513–2518.

Gatignol et al., "Bleomycin resistance conferred by a drug–binding protein", *FEBS Letters,* vol. 230, Nos. 1,2, 1988, pp. 171–175.

Jones et al., "A dominant nuclear streptomycin resistance marker for plant cell transformation", *Mol Gen Genet,* vol. 210, 1987, pp. 86–91.

Hille et al., "Bleomycin resistance: a new dominant selectable marker for plant cell transformation", *Plant Molecular Biology,* vol. 7, 1986, pp. 171–176.

Mulsant et al., "Phleomycin Resistance as a Dominant Selectable Marker in CHO Cells", *Somatic Cell and Molecular Genetics,* vol. 14, No. 3, 1988, pp. 243–252.

Hay et al., "American Type Culture Collection Catalogue of Cell Lines and Hybridomas," Sixth Edition, 1988, pp. 343–353.

Itoh et al. Developmental and Hormonal Regulation of Rice alpha–Amylase–gusA Fusion Genes in Transgenic Rice Seeds, *Plant Physiol.* (1995) 107:25–31.

Piruzyan et al. *Escherichia coli* gluxaose isomerase gene expression in transgenic plants. Chemical Abstracts vol. 110 No. 25.

Smith et al. Antisense RNA inhibition of polygalacturonase gene expression in transgenic tomatoes. *Natur* vol.. 334, pp. 724–726, Aug. 25, 1988.

Rosenfield et al. Cloning and characterization of the xyl gene from *E. coli. Mol. Gen. Genet.* (1984) 194:410–415.

Linsmaier et al., Organic Growth Factor Requirements of Tobacco Tissue Cultures, *Physiologia Plantarum,* 18:100–127 (1965).-

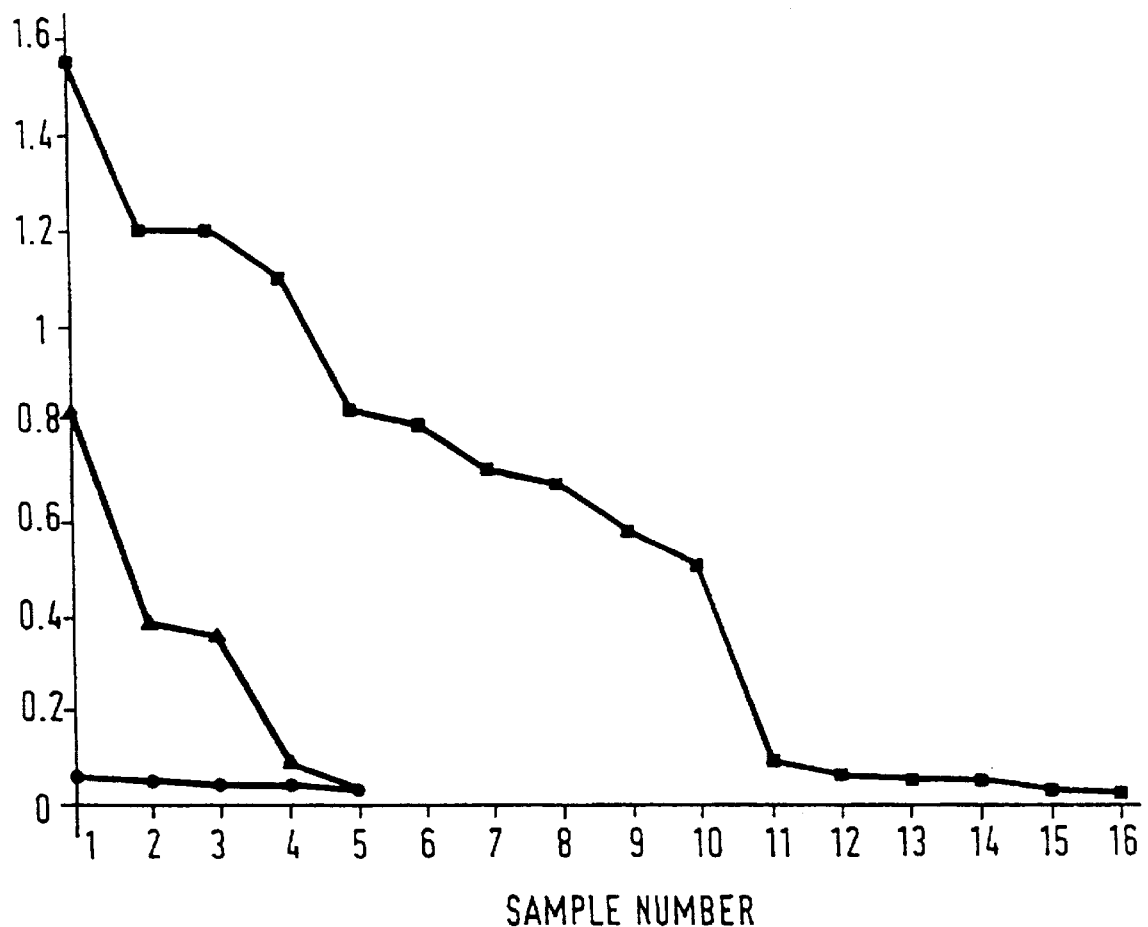

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1650 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 432..1607

(xi) SEQUENCE DESCRIPTION: SEQ ID NO:1:

```
ATCGATAACT TTCCACGCGA TGTCGCAGAG CTGGTGGACT GGTTCGACGC TCGCGACCCT    60

AACCGCATGT GCGCCCGGTG CCCGCTACGC GAGCAGATCC CGGTCTGGCT GTTGGGATCT   120

CTTGTCCTTC GAATTCGGCG ACGGAAACAT GTTCGCTGGT CAACAAGTAG TACTCGGTAT   180

CGTCCTTTTT GAGGGAAAA GGGTCTTGAT AAAAGAAGGG TTTGTTTGAC ATTGTGCTCT    240

CACTTACCGC TCGGTATGGT TATTCTCTGG GCAGGTGTTC CATTGCCCGA CTCAAAGCGA   300

GTAACACTAT CCTACACAAT TTTTTAACAA AAACTGAGAC AAGTACGACT TTTTACGCCC   360

GGAGGTTACT TCATGCGGGT TTCTTGGTTT AATACCTCCC ATTGATCTCC ACATTGAAAC   420
```

| | | | | | | | | | | | | | | |
|---|---|---|---|---|---|---|---|---|---|---|---|---|---|---|
| AGGGCTTGAT A ATG CAA AAA CTC ATT AAC TCA GTG CAA AAC TAT GCC TGG | | | | | | | | | | | | | 470 | |
| Met Gln Lys Leu Ile Asn Ser Val Gln Asn Tyr Ala Trp | | | | | | | | | | | | | | |
| 1 5 10 | | | | | | | | | | | | | | |

```
GGA AGT AAA ACT GCG TTA ACG GAA CTT TAT GGC ATC GCC AAT CCG CAG    518
Gly Ser Lys Thr Ala Leu Thr Glu Leu Tyr Gly Ile Ala Asn Pro Gln
         15                  20                  25

CAG CAG CCA ATG GCT GAA CTC TGG ATG GGC GCG CAT CCC AAA AGC AGC    566
Gln Gln Pro Met Ala Glu Leu Trp Met Gly Ala His Pro Lys Ser Ser
 30                  35                  40                  45

TCG CGA ATC ACC ACC GCC AAC GGC GAA ACC GTC TCC CTG CGT GAC GCC    614
Ser Arg Ile Thr Thr Ala Asn Gly Glu Thr Val Ser Leu Arg Asp Ala
                 50                  55                  60

ATC GAA AAG AAT AAA ACC GCC ATG CTG GGC GAA GCG GTA GCC AAC CGT    662
Ile Glu Lys Asn Lys Thr Ala Met Leu Gly Glu Ala Val Ala Asn Arg
             65                  70                  75

TTC GGC GAA CTG CCG TTT CTG TTT AAA GTA CTG TGC GCC GCC AAA CCG    710
Phe Gly Glu Leu Pro Phe Leu Phe Lys Val Leu Cys Ala Ala Lys Pro
         80                  85                  90

CTC TCT ATT CAG GTG CAC CCG AAT AAA CGC AAC TCC GAA ATC GGT TTC    758
Leu Ser Ile Gln Val His Pro Asn Lys Arg Asn Ser Glu Ile Gly Phe
     95                 100                 105

GCG AAA GAA AAT GCG GCG GGT ATC CCC ATG GAT GCC GCA GAG CGG AAC    806
Ala Lys Glu Asn Ala Ala Gly Ile Pro Met Asp Ala Ala Glu Arg Asn
110                 115                 120                 125

TAT AAA GAT CCT AAC CAT AAA CCA GAG CTG GTT TTT GCC CTG ACG CCT    854
Tyr Lys Asp Pro Asn His Lys Pro Glu Leu Val Phe Ala Leu Thr Pro
                130                 135                 140

TTC CTG GCG ATG AAC GCG TTC CGC GAA TTT TCT GAC ATT GTC TCT TTA    902
Phe Leu Ala Met Asn Ala Phe Arg Glu Phe Ser Asp Ile Val Ser Leu
            145                 150                 155

CTG CAA CCT GTC GCC GGC GCG CAT TCC GCT ATC GCC CAC TTT TTG CAG    950
Leu Gln Pro Val Ala Gly Ala His Ser Ala Ile Ala His Phe Leu Gln
        160                 165                 170

GTG CCG AAT GCT GAA CGT CTG AGC CAG CTT TTC GCC AGC CTG TTG AAT    998
Val Pro Asn Ala Glu Arg Leu Ser Gln Leu Phe Ala Ser Leu Leu Asn
    175                 180                 185

ATG CAA GGC GAA GAA AAA TCC CGC GCG TTA GCC GTA CTC AAA GCG GCG   1046
Met Gln Gly Glu Glu Lys Ser Arg Ala Leu Ala Val Leu Lys Ala Ala
190                 195                 200                 205

CTT AAC AGC CAG CAA GGC GAA CCG TGG CAA ACG ATC CGC GTG ATT TCA   1094
Leu Asn Ser Gln Gln Gly Glu Pro Trp Gln Thr Ile Arg Val Ile Ser
                210                 215                 220

GAG TAT TAT CCT GAC GAC AGC GGG CTT TTC TCT CCT TTG TTG CTG AAT   1142
Glu Tyr Tyr Pro Asp Asp Ser Gly Leu Phe Ser Pro Leu Leu Leu Asn
            225                 230                 235

GTG GTC AAA CTG AAT CCC GGC GAG GCG ATG TTC CTG TTT GCT GAA ACG   1190
Val Val Lys Leu Asn Pro Gly Glu Ala Met Phe Leu Phe Ala Glu Thr
        240                 245                 250
```

```
CCT CAT GCT TAT CTG CAG GGC GTT GCG CTG GAA GTC ATG GCG AAC TCC      1238
Pro His Ala Tyr Leu Gln Gly Val Ala Leu Glu Val Met Ala Asn Ser
    255                 260                 265

GAT AAC GTT CTG CGC GCT GGC CTT ACG CCA AAA TAT ATC GAC ATC CCT      1286
Asp Asn Val Leu Arg Ala Gly Leu Thr Pro Lys Tyr Ile Asp Ile Pro
270                 275                 280                 285

GAG CTG GTC GCG AAC GTG AAG TTC GAA CCT AAG CCT GCC GGC GAG TTG      1334
Glu Leu Val Ala Asn Val Lys Phe Glu Pro Lys Pro Ala Gly Glu Leu
                290                 295                 300

CTG ACT GCC CCG GTG AAA AGC GGC GCG GAG CTG GAC TTC CCA ATT CCG      1382
Leu Thr Ala Pro Val Lys Ser Gly Ala Glu Leu Asp Phe Pro Ile Pro
            305                 310                 315

GTT GAC GAT TTT GCT TTT TCA CTG CAC GAC CTG GCG CTT CAG GAG ACG      1430
Val Asp Asp Phe Ala Phe Ser Leu His Asp Leu Ala Leu Gln Glu Thr
        320                 325                 330

AGC ATC GGC CAA CAC AGC GCC GCG ATT CTG TTC TGC GTT GAG GGT GAG      1478
Ser Ile Gly Gln His Ser Ala Ala Ile Leu Phe Cys Val Glu Gly Glu
    335                 340                 345

GCG GTG TTA CGT AAA GAT GAA CAG CGT CTG GTA CTG AAG CCG GGT GAA      1526
Ala Val Leu Arg Lys Asp Glu Gln Arg Leu Val Leu Lys Pro Gly Glu
350                 355                 360                 365

TCT GCC TTT ATC GGC GCG GAT GAG TCT CCG GTT AAC GCC AGC GGC ACG      1574
Ser Ala Phe Ile Gly Ala Asp Glu Ser Pro Val Asn Ala Ser Gly Thr
                370                 375                 380

GGC CGT TTA GCG CGT GTT TAT AAC AAG CTG TAGCAACGTA CTGAATTTTT        1624
Gly Arg Leu Ala Arg Val Tyr Asn Lys Leu
            385                 390

TAACAACTCT TGCTAAGCTT ATCGAT                                         1650

(2) INFORMATION FOR SEQ ID NO:2:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Lys Leu Ile Asn Ser Val Gln Asn Tyr Ala Trp Gly Ser Lys
  1               5                  10                  15

Thr Ala Leu Thr Glu Leu Tyr Gly Ile Ala Asn Pro Gln Gln Gln Pro
                 20                  25                  30

Met Ala Glu Leu Trp Met Gly Ala His Pro Lys Ser Ser Ser Arg Ile
             35                  40                  45

Thr Thr Ala Asn Gly Glu Thr Val Ser Leu Arg Asp Ala Ile Glu Lys
         50                  55                  60

Asn Lys Thr Ala Met Leu Gly Glu Ala Val Ala Asn Arg Phe Gly Glu
 65                  70                  75                  80

Leu Pro Phe Leu Phe Lys Val Leu Cys Ala Ala Lys Pro Leu Ser Ile
                 85                  90                  95

Gln Val His Pro Asn Lys Arg Asn Ser Glu Ile Gly Phe Ala Lys Glu
                100                 105                 110

Asn Ala Ala Gly Ile Pro Met Asp Ala Ala Glu Arg Asn Tyr Lys Asp
            115                 120                 125

Pro Asn His Lys Pro Glu Leu Val Phe Ala Leu Thr Pro Phe Leu Ala
        130                 135                 140

Met Asn Ala Phe Arg Glu Phe Ser Asp Ile Val Ser Leu Leu Gln Pro
145                 150                 155                 160
```

```
Val Ala Gly Ala His Ser Ala Ile Ala His Phe Leu Gln Val Pro Asn
                165                 170                 175

Ala Glu Arg Leu Ser Gln Leu Phe Ala Ser Leu Leu Asn Met Gln Gly
            180                 185                 190

Glu Glu Lys Ser Arg Ala Leu Ala Val Leu Lys Ala Ala Leu Asn Ser
        195                 200                 205

Gln Gln Gly Glu Pro Trp Gln Thr Ile Arg Val Ile Ser Glu Tyr Tyr
    210                 215                 220

Pro Asp Asp Ser Gly Leu Phe Ser Pro Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Pro Lys Pro Ala Gly Glu Leu Leu Thr Ala
    290                 295                 300

Pro Val Lys Ser Gly Ala Glu Leu Asp Phe Pro Ile Pro Val Asp Asp
305                 310                 315                 320

Phe Ala Phe Ser Leu His Asp Leu Ala Leu Gln Glu Thr Ser Ile Gly
                325                 330                 335

Gln His Ser Ala Ala Ile Leu Phe Cys Val Glu Gly Glu Ala Val Leu
            340                 345                 350

Arg Lys Asp Glu Gln Arg Leu Val Leu Lys Pro Gly Glu Ser Ala Phe
        355                 360                 365

Ile Gly Ala Asp Glu Ser Pro Val Asn Ala Ser Gly Thr Gly Arg Leu
    370                 375                 380

Ala Arg Val Tyr Asn Lys Leu
385                 390

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AATACCTCCC ATAGATCTCC                                                    20

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CTTAGCAAGA GCTCTTAAAA AATTC                                              25
```

CARBON-BASED PROCESS FOR SELECTION OF TRANSGENIC PLANT CELLS

This application is a continuation of application Ser. No. 08/417,618, filed Apr. 6, 1995, now abandoned.

DESCRIPTION

1. Technical Field

The present invention relates to genetically transformed plants, and more particularly to a process for the selection of transformed plant cells cultured under heterotrophic conditions, as well as to transformed rooted plants and a kit for forming transformed plants.

2. Background Art

Techniques for selection of transgenic plant cells that are used currently involve the utilization of prokaryotic genes conferring resistance to toxic substances that are added to the regeneration medium, but that themselves are not essential for cell growth. These toxic additives are either antibiotics, herbicides, amino acids or amino acid analogs added in toxic concentrations. Although generally effective in selecting genetically modified plant cells, these systems have limitations. For example, they may not be effective in some types of plants, or they may result in abnormal phenotypes of the genetically engineered plants. Additionally, the use of these selective agents can have undesirable side effects and thus have raised public concern about their environmental safety.

Antibiotics such as kanamycin, G418, hygromycin, bleomycin and streptomycin, among others, have been used for selection of transgenic plants [(Bevan et al., *Nature*, 394:184–187 (1983); Dekeyser et al., *Plant Phys.*, 90:217–223 (1989); Hille et al., *Plant Mol. Biol.*, 7:171–176 (1986); Jones et al., *Mol. Gen. Gen.*, 210:86–91 (1987); Mulsant et al., *Som. Cell Mol. Gen.*, 14:243–252 (1988); Van den Elzen et al., *Plant Mol. Biol.*, 5:299–302 (1985); Waldron et al., *Plant Mol. Biol.*, 5:103–108 (1985)]. However, not all plants are equally sensitive to certain antibiotics. Kanamycin, which is used commonly, is not effective as a selective agent in gramineaceous plants; some plants from this group can tolerate up to 800 mg/L of kanamycin [Dekeyser et al., *Plant Phys.*, 90:217–223 (1989); Hauptmann et al., *Plant Physiol.*, 86:1216–1222 (1988)].

Additionally, there are negative aspects of antibiotic use, primarily, but not exclusively, due to their high toxicity against eukaryotic cells. For example, hygromycin has a broad spectrum of toxicity against prokaryotic and eukaryotic cells due to interference with protein synthesis [Waldron et al., *Plant Mol. Biol.*, 5:103–108 (1985)]. Bleomycin is a cytotoxic drug used in human cancer therapy and has known pulmonary toxicity [Gatignol et al., *FEBS Lett.*, 230:171–175 (1988); Hille et al., *Plant Mol. Biol.*, 7:171–176 (1986); Mulsant et al., *Som. Cell Mol. Gen.*, 14:243–252 (1988)]. Many antibiotics are also potent allergens. Thus, extensive use of antibiotics in routine selections of transgenic plants can pose a health hazard to the research staff. It is also possible that upon lysis of transgenic plant cells, the DNA encoding for the antibiotic resistance may be taken up by bacteria, rendering them antibiotic-resistant and thereby a threat to the public health.

Herbicides such as chlorsulfuron, 2,4-D, glyphosate, phosphinotricin, and others, have been proposed as selective agents [De Block et al., *EMBO J.*, 6:2513–2518 (1987); Dekeyser et al., *Plant Phys.*, 90:217–223 (1989); Li et al., *Plant Phys.*, 100:662–668 (1992); Streber et al., *Bio/Technology*, 7:811–816 (1989); Shah et al., *Science*, 233:478–481 (1986); White et al., *Nucl. Acid Res.*, 18:1062 (1990)]. The use of herbicide resistance in identification of transgenic plants can result in increased weediness of transgenic plants because they can become herbicide-resistant weeds in the alternate years of crop rotation. Out-crossing to wild relatives is also a concern. If the mechanism of resistance to the herbicide is based on detoxification, there is a potential for one or more of its metabolites to be toxic (Stalker, et al., *Science*, 242:419–423 (1988). Further, the use of herbicide-resistant crops probably will increase the herbicide load in the environment.

Certain amino acids such as lysine and threonine, or the lysine derivative amino ethyl cysteine (AEC), can also be used as selective agents due to their ability to inhibit cell growth when applied at high concentrations [Shaul et al., *The Plant J.*, 2:203–209 (1992); Perl et al., *Bio/Technology*, 11:715–718 (1993)]. In this selection system, expression of the selectable marker gene, which permits the transgenic cells to grow under selection, results in overproduction of amino acids by transgenic cells, which counteracts the selective pressure. In some cases, this results in abnormal plant development [Shaul et al., *The Plant J.*, 2:203–209 (1992)]. Moreover, transgenic plants that are selected in such a system have permanently altered amino acid composition, which may affect the nutritional value of the transgenic plants [Perl et al., *Bio/Technology*, 11:715–718 (1993)].

To be generally useful, a selectable marker must meet certain criteria. Selection must be stringent with a minimum of non-transformed plant tissue escaping the selection process. The selection should result in a large number of independent transformation events and not significantly interfere with regeneration. In addition, the marker should work well in a large number of plant species, and there should be an assay to score transformed tissue for confirmation that the marker gene is being expressed.

Another phenomenon associated with selectable markers is that once transformed plant cells are selected by means of the marker and rooted plants are regenerated, the marker continues to be expressed in the mature, autotrophically-grown plants. Thus, as was noted before, a transgenic plant can permanently express an altered amino acid composition or a gene for antibiotic resistance. It would be beneficial if once selected and regenerated, the autotrophic plants such as rooted plants expressed the marker to a lessened extent or not at all.

The present invention provides a process for selecting transformed plant cells that meets the above criteria, while avoiding toxic or environmentally unsafe substances. The present invention also provides a means by which expression of the selectable marker can be lessened or shut off in a rooted plant.

BRIEF SUMMARY OF THE INVENTION

The present invention contemplates a process for selectively growing transformed plant cells cultured under heterotrophic conditions. Also contemplated are a transformed plant whose genome contains an identifiable heterologous, exogenously supplied DNA segment that contains two expression cassettes. A kit useful for transforming plant cells is also contemplated.

Thus, in one embodiment, a selection process for transformed plant cells is contemplated. In accordance with this process, (a) a mixture of transformed and non-transformed plant cells is cultured under heterotrophic culture conditions in a culture medium that contains minimal nutrients required for growth and proliferation by those plant cells except for a source of carbon that is utilized to support that growth and proliferation. The source of carbon utilized is replaced by an encrypted or latent (growth-limiting) carbon source that does not support growth and proliferation by the non-transformed cells. The transformed cells of the mixture contain a genomic heterologous DNA segment that contains two expression cassettes, The first expression cassette contains a heterologous DNA selectable marker segment that includes (i) a first gene that encodes a heterologous enzyme that on expression converts the encrypted carbon source into a carbon source that supports growth and proliferation by the transformed plant cells under heterotrophic culture conditions. The first gene is operatively linked to (ii) a first promoter DNA segment that controls expression of the heterologous enzyme, and (iii) a termination DNA segment. The second expression cassette contains (i) a second gene that is expressed in a transformed plant, and that gene is operatively linked to (ii) a second promoter DNA segment that controls expression of that second gene and (iii) a termination DNA segment.

(b) The heterotrophic culture conditions are maintained for a time period sufficient for the transformed plant cells to express the heterologous enzyme, proliferate and grow. Inasmuch as the non-transformed plant cells cannot utilize the encrypted or latent carbon source, those cells do not grow and proliferate. The transformed cells that do grow and proliferate can thereby be selected from the non-transformed cells.

A particularly preferred first gene encodes the enzyme phosphomannose isomerase (pmi; EC 5.3.1.8) that converts non-utilizable mannose-6-phosphate into fructose-6-phosphate that can be used by plant cells as a carbon source to support cell growth and proliferation. The pmi gene is also known as mana, and this gene is often referred to herein as pmi/mana. The encrypted (growth-limiting) carbon source useful with this first gene is mannose. Another preferred useful gene encodes mannitol-1-oxidoreductase that converts mannitol into mannose, and here, mannitol is the encrypted (growth-limiting) carbon source. This second gene and its encrypted carbon source are used in plant cells that have previously been transformed with a pmi/mana gene. Another preferred first gene encodes human L-iditol dehydrogenase (EC 1.1.1.14) that converts sorbitol into fructose, so that sorbitol is used as the encrypted (growth-limiting) carbon source. Similar aldehyde reductase enzyme genes can also be used.

The proliferating cells so produced and selected can thereafter be regenerated by culture in appropriate media into mature plants via meristematic tissue or embryos, or via callus tissue conversion into meristematic tissue or embryos. Thus, the selected proliferating cells are preferably collected and thereafter regenerated into mature plants that grow autotrophically. The above process therefore more preferably utilizes the added steps of:

(c) recovering the selected proliferating cells; and (d) regenerating plants from those proliferating cells.

The promoter of the first expression cassette preferably is repressed by a product of the normal autotrophic metabolism of the transgenic plant, which product is also present in a non-transgenic plant. Exemplary preferred promoters include the cucumber malate synthase promoter, the cucumber isocitrate lyase promoter and the rice α-amylase Amy3A promoter.

The second gene can be any gene desired to be expressed in a plant, and its promoter and termination DNA segments can be any desired promoter and terminator that operate in plants.

A transgenic plant whose genome comprises a heterologous DNA segment that contains two expression cassettes is also contemplated.

The first expression cassette contains a heterologous DNA selectable marker segment that includes (i) a first gene that encodes a heterologous enzyme that on expression during heterotrophic culture of cells from the transformed plant converts an encrypted carbon source that does not support growth and proliferation of non-transformed plant cells of the same type into a carbon source that supports growth and proliferation of those transformed cells. That first gene is operatively linked to (ii) a promoter DNA segment that controls expression of the heterologous enzyme and (iii) a termination DNA segment. The second expression cassette contains (i) a second gene that is expressed in the transformed plant that is operatively linked to (ii) a second promoter DNA segment that controls expression of the second gene and (iii) a termination DNA segment.

The before-noted preferences are also followed for the first gene and its promoter in the transgenic plant. The second gene and its promoter are also as discussed before.

A kit for forming transformed plant cells is also contemplated. That kit comprises:

(a) a first package containing a DNA segment for transforming plant cells that contains an expression cassette operatively linked to a linker segment containing at least one restriction endonuclease site. The expression cassette contains a heterologous DNA selectable marker segment that includes (i) a first gene that encodes a heterologous enzyme that on expression during heterotrophic culture of transformed plant cells converts an encrypted carbon source that does not support growth and proliferation of non-transformed plant cells into a carbon source that supports growth and proliferation the transformed cells. The first gene is operatively linked to (ii) a promoter DNA segment that controls expression of the heterologous enzyme and (iii) a termination DNA segment. (b) A second package is also present that contains minimal nutrients required for growth and proliferation of plant cells during heterotrophic culture except for a source of carbon. That source of carbon is replaced by an encrypted carbon source that does not support growth and proliferation of non-transformed plant cells but does support growth and proliferation of a transformed plant cell whose genome contains the DNA segment of the first package. Instructions for use of the kit components are also preferably provided.

The present invention has several benefits and advantages.

One benefit of the invention is that its selective growth process does not rely upon potentially harmful antibiotics, weed killers or other possibly toxic materials.

One advantage of the invention is that its encrypted (growth-limiting) carbon source can be and preferably is a carbohydrate.

Another benefit of the invention is that expression of the selectable marker can be repressed in the regenerated plant under autotrophic growth conditions.

Another advantage of the invention is that the selectable marker first gene can be used with substantially any second expressed gene.

Still another benefit of the invention is that its kit provides a ready means for inserting a second expression cassette into a plant transforming vector and an appropriate selection medium for the enhanced transformation and selected growth of transformed plant cells.

Still another advantage is that successive transformations can be made in which one encrypted (growth-limiting) carbohydrate can be converted by a second selectable marker gene into another encrypted (growth-limiting) carbohydrate that is converted into a useful carbon source by a first selectable maker gene also present in the transformed cells.

Still further benefits and advantages of the present invention will be apparent to the skilled worker from the disclosure that follows.

BRIEF DESCRIPTION OF THE SEQUENCE LISTING

SEQ ID NO:1 is a sequence listing for the 1650 base pair ClaI fragment that contains the *Salmonella typhimurium* phosophomannose isomerase (pmi) gene.

SEQ ID NO:2 is the amino acid sequence for pmi.

SEQ ID NO:3 is the sequence of one of the primers used to facilitate the cloning of the pmi gene into a plant transformation vector. The primer corresponds to bases 391 to 410 of SEQ ID NO:1 with a substitution of an adenine for a thymine at base 403.

SEQ ID NO:4 is the sequence of the other primer used to facilitate the cloning of the pmi gene into a plant transformation vector. The primer corresponds to a complementary sequence to bases 1627 to 1651 of SEQ ID NO:1, with the substitution of a cytosine for a guanine at base 1638 and a cytosine for thymine at base 1640.

BRIEF DESCRIPTION OF THE DRAWINGS

FIG. 3 shows the relative NPTII expression in populations of plants selected on kanamycin and mannose with plants regenerated with no selection. Data for non-transformed plants (negative control) are shown as closed circles. Data for use of kanamycin (positive control) for selection of transformed plants are shown as closed triangles. Data for the transformed plants selected on mannose are shown as closed squares.

DETAILED DESCRIPTION OF THE INVENTION

A. Definition of Terms

Figure 1:
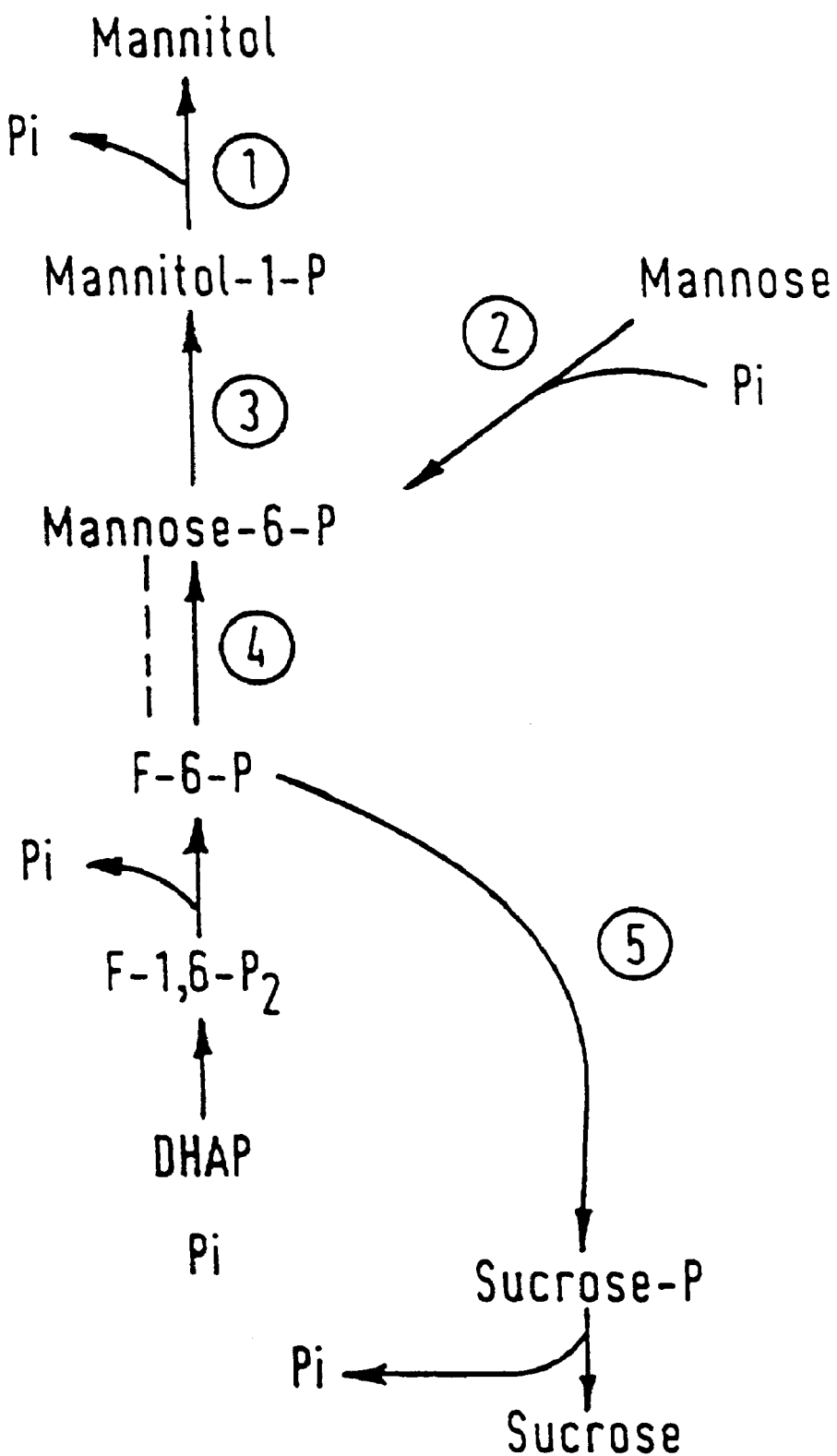
FIG. 1 shows the relationship between mannitol and sucrose biosynthesis in plants. Circled numbers identify enzymes that catalyze the reaction shown as follows: (1) mannitol-1-phosphate phosphatase, (2) mannose Kinase, (3) mannose-6-phosphate reductase, (4) mannose-6-phosphate isomerase, and (5) sucrose phosphate synthase.

Amino Acid: All amino acid residues identified herein are in the natural L-configuration. In keeping with standard polypeptide nomenclature, *J. Biol. Chem.*, 243:3557–59 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Autologous: A DNA segment or protein normally present in a non-transformed cell.

Explant: A piece of plant tissue.

Expression: The combination of intracellular processes, including transcription and translation undergone by a structural gene to produce a polypeptide.

Expression cassette: A DNA segment construct comprising a gene to be expressed operatively linked to a promoter DNA and to a DNA termination segment and sequences sufficient for translation, as well as any other regulatory signals needed to effect proper processing of the expression product.

Expression vector: A DNA sequence that forms control elements that regulate expression of a desired gene when operatively linked to that gene within a vector. An expression vector of particular interest also contains DNA segments that permit integration into the plant genome.

Gene: A sequence of nucleotides in the genome of an organism to which a specific function can be ascribed.

Heterologous: A DNA segment or protein not present in a non-transformed cell.

Integrated: A heterologous DNA sequence incorporated into a host chromosome is integrated.

Operatively linked or inserted: A first DNA sequence such as a promoter DNA sequence is operatively linked to a second DNA sequence such as a heterologous gene DNA sequence if the two are covalently bonded in correct reading frame and situated so that the promoter DNA sequence influences the transcription or translation of the heterologous gene DNA sequence.

Promoter: A recognition site on a DNA sequence or group of DNA sequences that provide an expression control element for a gene and to which RNA polymerase specifically binds and initiates RNA synthesis (transcription) of that gene.

Recombinant DNA molecule: A hybrid DNA sequence comprising at least two nucleotide sequences not normally found together in nature.

Same type or same strain plant: A plant of the same cross as or a clone of the untransformed plant.

Structural gene: A DNA sequence that through an RNA intermediate encodes for a polypeptide; i.e., an amino acid residue sequence.

Transgenic plant: A plant that contains chromosomally integrated heterologous or foreign DNA whose expression may be constitutive or regulatable.

Vector: A DNA molecule capable of replication in a cell and/or to which another DNA segment can be operatively linked so as to bring about replication of the attached segment. A plasmid is an exemplary vector.

B. Introduction

Higher plants (plants) in their adult (mature) forms are autotrophic organisms. Thus, mature plants use carbon dioxide for most or all of their carbon requirements. However, when grown in a culture medium, as cell suspensions, microspores, protoplasts or as explants (collectively referred to as plant cells in that each is from a plant and has a nucleus and cytoplasm surrounded by a membrane), the cultured plant cells are heterotrophic and require the provision of an external source of carbon as well as other nutrients. That carbon source is typically sucrose, glucose or another carbohydrate that can be readily metabolized by the growing cells so that they can grow, proliferate and differentiate, and then be regenerated into mature plants.

However, not all sources of carbon, including some carbohydrates, can be metabolized by cultured plant cells. Plants simply do not possess all of the necessary enzymes needed to convert many simple organic molecules into useful sources of carbon.

For example, mannose, a saccharide that is present in many mammalian glycoproteins cannot be utilized as a carbon source for many plants. Thus, as is illustrated hereinafter, mannose is taken up by tomato cells, for example, and is converted into mannose-6-phosphate, but mannose-6-phosphate cannot be utilized by tomato plant cells as a source of carbon for cell growth and proliferation.

The present invention utilizes the fact that plant cells cannot grow and proliferate using many small, carbon-containing compounds as a source of carbon during heterotrophic culture as a means of selectively growing transformed (genetically engineered) plant cells. This is accomplished, inter alia, by using a marker gene for cell transformation that converts a source of carbon that does not support cell growth and proliferation (a non-useful carbon source) into a carbon source that supports cell growth and proliferation (a useful carbon source).

Thus, when a mixture of transformed and non-transformed plant cells is cultured under heterotrophic culture conditions on a medium that contains a non-useful source of carbon that does not support cell growth and proliferation of non-transformed plant cells, referred to herein as an encrypted, latent or growth-limiting carbon source, only those plant cells grow and proliferentiate that are transformed with a selectable marker gene whose expressed product converts the encrypted carbon source into a useful source of carbon. This carbon source is encrypted (in code) because the plant dells cannot use it to grow and proliferate, and it is only after the selectable marker gene product that is present in the transformed calls decodes (decrypts) or acts upon that carbon source does it become useful to support growth and proliferation in the transformed plant cells.

C. The Process

In one embodiment, a selection process for transformed plant cells is contemplated. In accordance with this process, (a) a mixture of transformed and non-transformed plant cells is cultured under heterotrophic culture conditions in a culture medium that contains minimal nutrients required for proliferation and differentiation by those plant cells except for a useful source of carbon. The normally present useful source of carbon is replaced by an encrypted, latent or growth-limiting carbon source that does not support growth and proliferation of the non-transformed cells. The transformed cells of the mixture contain a genomic (chromosomally integrated) heterologous DNA segment that contains two expression cassettes.

The first expression cassette contains a heterologous DNA selectable marker segment that includes (i) a first gene that encodes a heterologous enzyme that on expression converts the encrypted carbon source into a useful carbon source that supports growth and proliferation of the transformed plant cells under heterotrophic culture conditions. That first gene is operatively linked to (ii) a first promoter DNA segment that controls expression of the heterologous enzyme, and (iii) a termination DNA segment. The second expression cassette contains (i) a second gene that is expressed in a transformed plant, and that second gene is operatively linked to (ii) a second promoter DNA segment that controls expression of that second gene and (iii) a termination DNA segment.

(b) The heterotrophic culture conditions are maintained for a time period sufficient for the transformed plant cells to express the heterologous enzyme, grow and proliferate. The non-transformed plant cells do not utilize the encrypted or latent carbon source and do not grow and proliferate. The transformed cells that do grow and proliferate are thereby selected away from the non-transformed cells, and are preferably collected for regeneration into plants.

The first expression cassette DNA thus contains three operatively linked elements: (1) a first gene that encodes a heterologous enzyme that converts an encrypted carbon source into a useful carbon source, (2) a first promoter DNA segment that controls the expression of that heterologous enzyme, and (3) a first termination DNA segment that causes termination of transcription and polyadenylation of the 3'-end of the translated RNA.

In some cases, a gene that is functionally similar or identical to the first gene of the first expression cassette is present in the genome of the non-transformed plant. That endogenous gene is, however, functionally not present in the heterotrophically cultured plant cells inasmuch as the non-transformed plant cells do not grow and proliferate using the same encrypted carbon source that the heterologous enzyme product of that first gene converts into a useful carbon source. This concept is exemplified by the fact that tomato plants do not grow and proliferate when heterotrophically cultured using either lactose or salicin as carbon sources. Lactose is susceptible to cleavage by a β-galactosidase into glucose and galactose, whereas salicin can be cleaved by a β-glucosidase to form glucose. Nonetheless, one commercially available β-galactosidase is recovered from jack beans, whereas a commercially available β-galactosidase is recovered from sweet almonds (Sigma Chemical Co.), indicating that the plant genomes contain genes for each enzyme that are not sufficiently expressed at all times.

The choice of the first gene depends upon its encoded enzyme and the function of that enzyme, which is to convert an encrypted, non-useful carbon source into a useful carbon source that supports the growth and proliferation of heterotrophically-cultured transgenic plant cells. Continuing this choice of the first gene backwards, one assays carbon sources that the plant cells to be transformed cannot utilize to grow and proliferate.

Such an assay is readily carried out by culturing the desired non-transformed plant cells in a medium that contains minimal nutrients required for cell growth and proliferation except for a source of carbon. Such media are well know in the art and are exemplified by the well known medium of Murashigi and Skoog, *Physiol. Plant,* 15:437–498(1962); MS salts. The glucose or sucrose usually present in that medium is replaced with the carbon source to be assayed that is present at about the same concentration as was the glucose or sucrose.

The plant cells are then cultured in the resulting medium following usual procedures. An assayed carbon source that does not support growth and proliferation of the heterotrophically cultured cells is determined. Exemplary carbon sources that do not support the growth and proliferation of the illustrative tomato cells used herein include mannose, mannitol, sorbitol, lactose and salicin. In addition, oat, maize, melon and squash cells are shown not to grow and proliferate using mannose as the sole carbon source.

An enzyme is then selected that converts the non-utilizable carbon source into a carbon source that can be utilized by the plants. Exemplary sources of carbon that can be used by plant cells to support growth and proliferation are the compounds of the Calvin cycle and include glucose, fructose, ribulose and glyceric acid, as well as the compounds of the Hatch-Slack pathway that include oxaloacetate, malate and pyruvate. Thus, supplying the heterotrophically cultured plant cells with one of the beforementioned carbon sources and the other required minimal nutrients of the medium results in growth and proliferation of the plant cells in that the plant cells contain endogenous enzymes that utilize such compounds for growth and proliferation.

Inasmuch as living organisms all utilize carbon sources for growth and proliferation, many such enzymes are available for use. An enzyme that converts a non-useful carbon source to a useful 6-carbon source such as glucose or fructose is preferred, and such enzymes are utilized illustratively herein.

One preferred enzyme used illustratively herein is phosphomannose isomerase (pmi/manA; E.C. 5.3.1.8) that converts mannose-6-phosphate into fructose-6-phosphate that supports plant cell growth and proliferation. Mannose-6-phosphate is formed when mannose is used as the encrypted carbon source. This gene is designated as the pmi gene in *Rhizobium meliloti* (*Gene,* 122: 35–43), *Pseudomonas aeruginosa* (*Gene,* 42:293–302), Saccharomyces cerevisiae (*Molecular and Cellular Biology,* 12:2924–2930) and *Salmonella typhimurium* (*Gene,* 103:135–136). In *Escherichia coli,* the phosphomannose isomerase gene is called manA (*Gene,* 32:41–48).

Another useful enzyme is L-iditol dehydrogenase (EC 1.1.1.14) that converts sorbitol into fructose. Several aldehydoreductase enzymes are known that can be used to convert sorbitol as encrypted carbon source into the useful carbon source glucose. One exemplary enzyme is D-sorbitol 1-oxidoreductase (EC 1.1.00.24). Lactase (EC 3.2.1.108) that converts the encrypted carbon source lactose into glucose and galactose, as do several other β-galactosidases, and α,α-trehalase (EC 3.2.1.28) that converts the encrypted carbon source α,α-trehalose into glucose is yet another useful enzyme.

Upon determination of the heterologous marker enzyme for use, the gene that encodes that enzyme is obtained. The genes that encode many heterologous marker enzymes have been reported in the literature and can be obtained from the authors, as was the case of the pmi gene used here. Many useful gene sequences are also reported in the GenBank database such as the human L-iditol dehydrogenase gene (GenBank accession number L29008) or the rat aldehyde reductase genes (GenBank accession numbers X74673 and D10484) or the human aldehyde reductase gene (GenBank accession number J04794). Sequences for several useful β-galactosidases are also available in the GenBank data base. For example, the enzyme from *Brassica oleracea* has accession Number X84684, that of the Granny Smith apple (*Malus domestica*) has accession Number L29451, and three genes from *E. coli* have the accession Numbers X03228, M13700 and M13797. The sequence of the *S. typhimurium* pmi gene used illustratively here has GenBank accession Number X57117.

Where the desired gene is unavailable, but its sequence is known, PCR technology can be used with a DNA or RNA prepared from a source reported or otherwise known to express the gene to obtain a useful copy of that gene.

Where a sequence of a desired gene is not available, the enzyme itself is obtained following usual procedures, and its termini are sequenced sufficiently so that sets of redundant DNA probes can be prepared and used with PCR technology to obtain a cDNA copy of the gene from a DNA or RNA library of the organism from which the enzyme was isolated. Of course, if the amino acid residue sequence of that desired enzyme is known, sequencing is unnecessary.

The preparation and use of DNA and RNA libraries for obtaining desired genes from host organisms is well known in this art and will not be dealt with further herein.

The DNA segment encoding the heterologous selectable marker enzyme (first gene) is typically isolated and purified containing appropriate endonuclease restriction sites at the 5'- and 3'-termini so that that gene can be operatively linked to the promoter and termination DNA segments. If that DNA segment is not so obtained, suitable restriction sites can be added by simple ligation or in vitro mutagenesis is well known.

An above-described first gene is operatively linked to a promoter DNA segment. That promoter is, of course, a promoter segment that is operative in plant cells. Exemplary useful promoters include the constitutive CaMV 35S promoter of the cauliflower mosaic virus, the octopine synthase promoter (P-Ocs) and the nopaline synthase promoter (P-Nos) that are constitutive promoters.

In one embodiment, the promoter utilized is repressed by a product of the normal metabolism of the transgenic (or non-transgenic) plant cultured under autotrophic growth conditions. Thus, once a mature plant has been regenerated, and selection is no longer necessary, the promoter controlling expression of the marker enzyme is shut off or repressed so that none or a reduced amount of the selecting enzyme is expressed.

An exemplary promoter whose activity is repressed by a normal product of plant metabolism is the Rice α-amylase Amy3A promoter [Thomas et al., *Plant Physiol.,* 106:1235–1239(1994)]. Expression from this α-amylase in rice is repressed by the presence of sucrose, a product of the normal, autotrophic, metabolism of both transformed and non-transformed rice cells.

Two additional promoters that are repressible by normal products of plant metabolism are the cucumber malate synthase and isocitrate lyase promoters reported in Graham et al., *Plant Cell,* 6: 761–772 (1994). Glucose, fructose and raffinose in culture media repressed both promoters. Inasmuch as the malete synthase promoter is repressed when plant cells are heterotropically cultured in the presence of mannose, that promoter is not utilized in conjunction with the pmi/manA gene and mannose as the first encrypted carbon source.

The final element of the first cassette is a first termination DNA segment that is operatively linked to the 3'-end of the first gene. Several termination segments useful in plants are well known and can be used herein. One exemplary segment is the 3'-non-translated region of the nopaline synthase gene [Nos-T; Fraley et al., *Proc. Natl. Acad. Sci. USA*, 80:4803–4807(1983)] used herein. Another is the 3'-non-translated region of the pea rbcS-E9 gene [E9; Coruzzi et al., *Embo J.*, 3:1671–1679(1984)].

The promoter and termination DNA segments are also preferably terminated by appropriate endonuclease restriction sites for ligation and operable linkage to the termini of the first gene and ligation to the second expression cassette as part of the genomic heterologous DNA segment, and also into an appropriate vector. Blunt end ligation can also be used for operative linking to the first gene and/or a vector.

The second expression cassette contains a second gene that is expressed in a transformed plant. That second or target gene encodes the protein whose presence, and usually expression, in a transformed plant is the rationale for transforming the plant.

The second gene can be any gene that is desired. Exemplary genes include those listed in Table I, below, whose transformations into plants have been disclosed in the patent citations shown in that Table.

TABLE 1

| Second Gene Product | Citation |
| --- | --- |
| Antibody | U.S. Pat. No. 5,202,422 |
| Mammalian Peptide | WO 87/00865 |
| HMG-CoA Reductase | U.S. Pat. No. 5,306,862 |
| Phosphofructokinase | U.S. Pat. No. 5,387,756 |
| Waxy Locus of Wheat (Antisense) | U.S. Pat. No. 5,365,016 |
| ADP-Glucose pyrophosphorylase, antisense | EP 0 368 506 A2 |
|  | EP 0 455 316 A2 |
|  | WO 92/11382 |
| Potato L-amylase | EP 0 470 145 B1 |
| Sucrose phosphate Synthase | EP 0 466 995 A2 |
|  | EP 0 530 978 |
| *E. coli* inorganic pyrophosphorylase | EP 0 485 044 A2 |
| Maize 1,4-α-glucan branching enzyme, antisense | WO 92/11375 |
| Granule-bound starch synthase, antisense | WO 92/11376 |
| Tomato vacuolar invertase, antisense | WO 92/14831 |
| *E. Herbicola* genes in the carotenoid synthetic pathway | WO 91/13078 |

The second gene is operatively linked to a second promoter DNA segment that controls expression of the second gene. This promoter is not repressed by a product of normal plant metabolism, and can be a constitutive promoter such as the CaMV 35S, P-Ocs and P-Nos promoters discussed before, or an organ-enhanced promoter that causes expression in one or more limited organs of the transformed plant.

Expression in one or more preselected organs with little or no expression in other organs such as roots versus leaves or stems is referred to herein as enhanced or preferential expression. An exemplary promoter that directs expression in one or more preselected organs as compared to another organ at a ratio of at least 5:1 is defined herein as an organ-enhancer promoter. Expression in substantially only one organ and substantially no expression in other organs is referred to as organ-specific expression; i.e., a ratio of expression products in a organ relative to another of about 100:1 or greater indicates organ specificity. Organ-specific promoters are thus members of the class of organ-enhanced promoters.

The CaMV 35S promoter is normally deemed to be a constitutive promoter. However, recent research has shown that a 21-bp region of the CaMV 35S promoter, when operatively linked into another, heterologous usual green tissue promoter, the rbcS-3A promoter, can cause the resulting chimeric promoter to become a root-enhanced promoter. That 21-bp sequence is disclosed in U.S. Pat. No. 5,023,179, whose disclosures are incorporated by reference. The chimeric rbcS-3A promoter containing the 21-bp insert of U.S. Pat. No. 5,023,179 is a useful root-enhanced promoter.

A similar root-enhanced promoter, that includes the above 21-bp segment is the −90 to +8 region of the CaMV 35S promoter itself. U.S. Pat. No. 5,110,732, whose disclosures are incorporated by reference, discloses that truncated CaMV 35S promoter provides enhanced expression in roots and the radical of seed, a tissue destined to become a root. That promoter is also useful.

Another useful root-enhanced promoter is the −1616 to −1 promoter of the oil seed rape (*Brassica napus*) gene disclosed in PCT/GB92/00416 (WO 91/13922 published Sep. 19, 1991). *E. coli* DH5α harboring plasmid pRlambdaS4 and bacteriophage lambdaβ1 that contain this promoter were deposited at the National Collection of Industrial and Marine Bacteria, Aberdeen, GB on Mar. 8, 1990 and have accession numbers NCIMB40265 and NCIMB40266. A useful portion of this promoter can be obtained as a 1.6–1.0 kb fragment by cleavage of the plasmid with HaeIII.

A root-enhanced promoter is the mannopine synthase (P-Mas) promoter present in plasmid pKan2 described by DiRita and Gelvin, *Mol. Gen. Genet.*, 207:233–241 (1987). This promoter is removable from its plasmid pKan2 as a XbaI fragment.

A mannopine synthase root-enhanced promoter is comprised of the core mannopine synthase (Mas) promoter region up to position −138 and the mannopine synthase activator from −318 to −213, and is collectively referred to as AmasPmas. This promoter has been found to increase production in tobacco roots about 10- to about 100-fold compared to leaf expression levels. The constitutive CaMV 35S promoter exhibits about one-half the expression of AmasPmas in tobacco, and expresses well in leaf tissue.

Another preferred root specific promoter is the about 500 bp 5' flanking sequence accompanying the hydroxyproline-rich glycopeprotein gene, HRGPnt3, expressed during lateral root initiation and reported by Keller et al., *Genes Dev.*, 3:1639–1646 (1989). Another preferred root-specific promoter is present in the about −636 to −1 5' flanking region of the tobacco root-specific gene ToRBF reported by Yamamoto et al., *Plant Cell*, 3:371–381 (1991). The cis-acting elements regulating expression were more specifically located by those authors in the region from about −636 to about −299 5' from the transcription initiation site. Yamamoto et al. reported steady state mRNA production from the ToRBF gene in roots, but not in leaves, shoot meristems or stems.

Still another useful storage organ-specific promoter are the 5' and 3' flanking regions of the fruit-ripening gene E8 of the tomato, *Lycopersicon esculentum*. These regions and their cDNA sequences are illustrated and discussed in Deikman et al., *EMBO J.*, 7(11):3315–3320 (1988) and *Plant Physiol.*, 100:2013–2017 (1992).

Three regions are located in the 2181 bp of the 5' flanking sequence of the gene and a 522 bp sequence 3' to the poly (A) addition site appeared to control expression of the E8 gene. One region from −2181 to −1088 is required for activation of E8 gene transcription in unripe fruit by ethylene and also contributes to transcription during ripening. Two further regions, −1088 to −863 and −409 to −263, are unable to confer ethylene responsiveness in unripe fruit but are sufficient for E8 gene expression during ripening.

The maize sucrose synthase-1 (Sh) promoter that in corn expresses its controlled enzyme at high levels in endosperm, at much reduced levels in roots and not in green tissues or pollen has been reported to express a chimeric reporter gene, β-glucuronidase (GUS), specifically in tobacco phloem cells that are abundant in stems and roots. Yang et al., *Proc. Natl. Acad. Sci., USA,* 87:4144–4148 (1990). This promoter is thus useful for plant organs such as fleshy fruits like melons, e. g. cantaloupe, or seeds that contain endosperm and for roots that have high levels of phloem cells.

Another exemplary tissue-specific promoter is the lectin promoter, which is specific for seed tissue. The lectin protein in soybean seeds is encoded by a single gene (Le1) that is only expressed during seed maturation and accounts for about 2 to about 5 percent of total seed mRNA. The lectin gene and seed-specific promoter have been fully characterized and used to direct seed specific expression in transgenic tobacco plants. See, e.g., Vodkin et al., *Cell,* 34:1023 (1983) and Lindstrom et al., *Developmental Genetics,* 11:160 (1990).

A particularly preferred tuber-specific expression promoter is the 5' flanking region of the potato patatin gene. Use of this promoter is described in Twell et al., *Plant Mol. Biol.,* 9:365–375 (1987). This promoter is present in an about 406 bp fragment of bacteriophage LPOTI. The LPOTI promoter has regions of over 90 percent homology with four other patatin promoters and about 95 percent homology over all 400 bases with patatin promoter PGT5. See, also, Wenzler et al., *Plant Mol. Biol.,* 12:41–50 (1989).

Still further organ-enhanced and organ-specific promoter are disclosed in Benfey et al., *Science,* 244:174–181 (1988).

The final element in the second expression cassette is a termination DNA segment. Any termination segment can be used, as was discussed before in regard to the first cassette.

The elements of the second expression cassette are operatively linked together, usually via ligated endonuclease sites, although blunt end ligation can also be utilized, as before.

It is also noted that either or both of the heterologous enzyme encoded by the first gene and the product of the second gene can be portions of a polyprotein that actually contains two or more proteins, e.g. enzymes, linked together by a peptide bond as has been found for several viral genes. See, for example, Vardi et al., *Proc. Natl. Acad. Sci. USA,* 90:7413–7417(1993) and Maiti et al., *Proc. Natl. Acad. USA,* 90:6110–6114(1993).

The first and second expression cassettes are linked together in the genomic heterologous DNA segment so that the two expression cassettes constitute very tightly linked loci that are transformed into the plant's chromosomal DNA. Thus, as is the case with other selectable marker systems, transformation of plant cells with one of the cassettes is very strongly correlated with transformation with the other. In this instance, growth and proliferation of cells that were putatively transformed indicates that the transformation with the second cassette was successful.

Use of the DNA segment containing the two linked expression cassettes to transform plant cells is discussed in detail hereinafter.

In some instances, it is desirable to transform plant cells on two separate occasions. Such double transformations require the use of two selectable markers and two target genes desired to be expressed. In the terminology used herein, such a double transformation utilizes four expression cassettes and two encrypted (growth-limiting) sources of carbon for heterotrophic growth. Two heterologous genomic DNA segments are present in the twice-transformed plants.

For ease of discussion as to this embodiment, the first and second expression cassettes are those already discussed, and those expression cassettes are present in the first-named genomic heterologous DNA segments. A second genomic heterologous DNA segment is also present in a twice-transformed plant and contains a third and a fourth expression cassettes.

The third expression cassette contains a second heterologous DNA selectable marker segment that includes (i) a second gene that encodes a second heterologous enzyme that is operatively linked to (ii) a third promoter DNA sequence that controls the expression of the second heterologous enzyme and (iii) a termination DNA segment.

The third promoter DNA can be and preferably is the same promoter used with the first gene that encodes a heterologous enzyme. The termination DNA segment is also any termination segment useful in plants as is also discussed before. The third promoter and this termination DNA segment are linked as discussed previously.

The second gene that encodes a second heterologous enzyme is different from those genes discussed before. The second heterologous enzyme converts a second encrypted carbon source into the first-named encrypted carbon source that supports growth and proliferation of the transformed plant cells. That second encrypted carbon source also does not support growth and proliferation of non-transformed plant cells of the same type.

Thus, the second encrypted carbon source can be viewed as a precursor to the first-named encrypted carbon source that is converted into a useful source of carbon to support cell growth and proliferation by the first heterologous enzyme. More specifically, where mannose is illustratively the first encrypted carbon source and phosphomannose isomerase is the first heterologous enzyme, mannitol can be used as the second encrypted carbon source along with mannitol 1-oxidoreductase as the second heterologous enzyme.

Thus, plant cells transformed with a first and second expression cassette containing the pmi/manA gene as a first gene selectable marker are transformed again with third and fourth expression cassettes whose third expression cassette contains a gene that encodes the mannitol 1-oxidoreductase gene and whose fourth cassette contains another desired gene. The resulting mixture of twice-transformed and once-transformed plant cells is heterotrophically cultured in a minimal nutrient medium that contains mannitol as the carbon source. Inasmuch as only the twice transformed cells contain a gene encoding mannitol 1-oxidoreductase and phosphomannose isomerase, only those cells grow and proliferate because they convert mannitol to mannose and mannose into fructose-6-phosphate.

Those proliferating twice-transformed cells are preferably recovered and regenerated into mature plants as discussed elsewhere.

It is noted that reference herein to "first", "second", "third" and "fourth" is for convenience only. Thus, the second cassette can be upstream of the first cassette, as can the fourth cassette be upstream of the third cassette.

Recombinant DNA Molecules

A recombinant DNA molecule useful herein can be produced by operatively linking a vector to an isolated heterologous DNA segment that contains two expression cassettes to form a plasmid. Particularly preferred recombinant DNA molecules are discussed in detail in the examples, hereafter. Vectors capable of directing the expression of the gene are referred to herein as "expression vectors".

In one preferred embodiment, a vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art.

Those vectors that include a prokaryotic replicon can also include a prokaryotic promoter region capable of directing the expression of gene in a host cell, such as *E. coli*, transformed therewith. Promoter sequences compatible with bacterial hosts are typically provided in plasmid vectors containing one or more convenient restriction sites for insertion of a DNA segment of the present invention. Typical of such vector plasmids are pUC18, pUC19, and pBR322 available from Gibco BRL, Gaithersburg, Md., and pPL and pKK223-3 available from Pharmacia, Piscataway, N.J. These vectors are utilized in the synthesis of the DNA segments present in the integrating expression vectors.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). These vectors are plant integrating vectors in that on transformation, a portion of the vectors' DNA is integrated into the genome of the host plant. For integrating vectors based on the Ti plasmid, the region integrated into the host plant chromosomes is that between the right and left borders of the Ti plasmid, or TDNA.

A preferred plant transformation vector useful herein is vector BIN19 [Bevan, *Nucleic Acids Res.*, 12:8711–8721 (1984)]. Other exemplary *A. tumefaciens* vectors useful herein are plasmids pKYLX6 and pKYLX7 of Schardl et al., *Gene*, 61:1–11 (1987) and Berger et al., *Proc. Natl. Acad. Sci. USA*, 86:8402–8406 (1989). Another useful vector herein is plasmid pBI101 that is available from Clontech Laboratories, Inc., Palo Alto, Calif. Plasmids BIN19, pKYLX7, pKYLX71 and pBI101 are binary vectors that are used in *A. tumefaciens*.

Another plant transformation system is based on *Agrobacterium rhizogenes* that induces hairy roots rather than a tumor on transformation. Application PCT/US87/02512 (WO 88/02405 published Apr. 7, 1988) describes the use of *A. rhizogenes* strain A4 and its Ri plasmid along with *A. tumefaciens* vectors pARC8 or pARC16 to transform the cucumber *Cucumis sativas*, cv, Straight Eight, and form regenerated cucumber plants.

An Agrobacterium-based transformation system for melon, another member of the cucumber family of Cucurbitaceae, *Cucumis melo* was reported by Dong et al., *Bio/Technology*, 9:858–863 (1991). Those workers used a binary vector that utilized the constitutive CaMV 35S promoter, and found evidence of transformation via a reporter gene in substantially all tissues examined. That work illustrates the amenability of melons to transformation via *A. tumefaciens*.

A variety of methods has been developed to operatively link DNA segments into vectors via complementary cohesive termini or blunt ends. In addition, synthetic linkers containing a variety of restriction endonuclease sites are commercially available from a number of sources including New England BioLabs, Beverly, Mass. These methods and use of synthetic linkers are well know in the art and will not be discussed further here. See Sambrook et al., *Molecular Cloning*, 2ed; Cold Spring Harbor Laboratory Press (1989).

Introducing genes into higher plants

Methods for transforming higher, multicellular flowering plants include Agrobacterium-mediated plant cell transformation, protoplast transformation, gene transfer into pollen, injection into reproductive organs, transformation of microspores and injection into immature embryos. Each of these methods has distinct advantages and disadvantages. Thus, one particular method of introducing genes into a particular plant species may not necessarily be the most effective for another plant species, but it is well known which methods are useful for a particular plant species.

Agrobacterium-mediated transfer is a widely applicable system for introducing genes into plant cells because the DNA can be introduced into whole plant tissues, thereby bypassing the need for regeneration of an intact, mature, plant from a protoplast. The use of Agrobacterium-mediated expression vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is within by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors such as those discussed before are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where Agrobacterium-mediated transformation is efficient; i.e., in dicotyledonous plants, it is a perferred method of choice because of the facile and defined nature of the gene transfer. However, few monocots such as cereals and grasses appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Commercially important cereal grains such as rice, corn, oats and wheat are usually transformed using alternative methods.

Agrobacterium-mediated transformation of leaf disks and other tissues such as callus appears to be limited to plant species that Agrobacterium infects. Thus, Agrobacterium-mediated transformation is most efficient in dicotyledonous plants, and dicotyledonous plants are a preferred source of the cells transformed here. Particularly preferred dicotyledonous plants include those of Brassicaceae (cabbage and broccoli), Compositae (lettuce), Umbelliferae (carrots), Solanaceae (pepper and tomato) and Cucurbitaceae (melon and squash) families of higher plants. However, as mentioned above, the transformation of asparagus using a monocot Acrobacterium can also be achieved.

Transformation of plant protoplasts can be achieved using methods based on calcium phosphate precipitation, polyethylene glycol treatment, electroporation, and combinations of these treatments. See, for example, Potrykus et al., *Mol. Gen. Genet.,* 199:183 (1985); Lorz et al., *Mol. Gen. Genet.,* 199:178 (1985); Fromm et al., *Nature,* 319:791 (1986); Uchimiya et al., *Mol. Gen. Genet.,* 204:204 (1986); Callis et al., *Genes and Development,* 1:1183 (1987); Marcotte et al., *Nature,* 335:454 (1988); Wang et al., *Bio/Technology,* 10:691–696 (1992); and Fennell et al., *Plant Cell Reports,* 11:567–570 (1992).

Application of these systems to different plant species depends upon the ability to regenerate that particular plant species from protoplasts. Illustrative methods for the regeneration of cereals from protoplasts are described in Fujimura et al., *Plant Tissue Culture Letters,* 2:74 (1985); Toriyama et al., *Theor Appl. Genet.,* 73:16 (1986); Yamada et al., *Plant Cell Rep.,* 4:85 (1986); Abdullah et al., *Biotechnology,* 4:1087 (1986). U.S. Pat. No. 4,634,674 teaches regeneration of tomato plants from protoplasts.

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology,* 6:397 (1988). In addition, "particle gun" or high-velocity microprojectile technology can be utilized. Using such technology, DNA is carried through the cell wall and into the cytoplasm on the surface of small metal particles as described in Klein et al., *Nature,* 327:70 (1987); Klein et al., *Proc. Natl. Acad. Sci. U.S.A.,* 85:8502 (1988); and McCabe et al., *Biotechnology,* 6:923 (1988); and Vasil et al., *Bio/Technology,* 9:667–674 (1992). The metal particles penetrate through several layers of cells and thus allow the transformation of cells within tissue explants.

Metal particles have been used to successfully transform corn (maize) and wheat cells and to produce fertile, stably transformed tobacco and soybean plants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology,* 101:433 (1983); D. Hess, *Intern Rev. Cytol.,* 107:367 (1987); Luo et al., *Plant Mol. Biol. Reporter,* 6:165 (1988). Expression of transformed genes can be obtained following injection of the DNA into reproductive organs of a plant as described by Pena et al., *Nature,* 325:274 (1987). U.S. Pat. No. 5,302,523 teaches transformation of maize cells using whisker bodies to penetrate the cells. DNA can also be injected directly into the cells of immature embryos and during the rehydration of desiccated embryos as described by Neuhaus et al., *Theor. Apl. Genet.,* 75:30 (1987); and Bedbrook et al., in *Proceedings Bio Expo 1986,* Butterworth, Stoneham, Mass., pp. 27–54 (1986), as well as by poly(ethylene glycol) or electroportation into maize microspores from which dihaploid homozygous plants can be regenerated. Fennell et al., *Plant Cell Reports,* 11:567–570 (1992).

The regeneration of plants from transformed plant cells such as either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

Growth media for plant cells contemplated herein are those familiar to workers of ordinary skill in these arts except that an encrypted carbon source is used in place of a usually used carbon source such as glucose or sucrose. Exemplary media contain Murashige and Skoog (MS) salts and RO vitamins. Regeneration media are similarly well known and also contain plant hormones such as benzyladenine, giberellic acid, indoleacetic acid, naphthylacetic acid, zeatine, thiamine hydrochloride and the like, and utilize an encrypted carbon source.

One special feature of a preferred nutrient medium for regeneration is that about 1.5 to about 3 times the usual amount of phosphorous is present as a water-soluble phosphate salt. The basis for this preference is the unexpected finding that an enhanced number of regenerated shoots were obtained using the enhanced amount of phosphate salt as well as a greater percentage of normal shoots among those regenerates.

The regeneration of plants containing the foreign gene introduced by Agrobacterium from leaf explants can be achieved as described by Horsch et al., *Science,* 227:1229–1231 (1985). In this procedure, transformants are grown in the presence of the appropriate encrypted carbon source in a medium that induces the regeneration of shoots in the plant species being transformed as described by Fraley et al.,*Proc. Natl. Acad. Sci. U.S.A.,* 80:4803 (1983). This procedure typically produces shoots within two to four months and these transformant shoots are then transferred to an appropriate root-inducing medium and an antibiotic to prevent bacterial growth.

Transformation of a plant cell suspension is preferred herein. Specific examples of such transformations are discussed hereinafter.

Transformant shoots that rooted in the presence of an encrypted carbon source to form plantlets are then transplanted to soil or other media to allow the production of roots. These procedures vary depending upon the particular plant species employed, such variations being well known in the art.

Genetics

A transgenic plant formed using Agrobacterium transformation methods can contain a single transgene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant hemizygote. A transgenic plant formed using Agrobacterium is referred to as a hemizygote.

More preferred is a transgenic plant that is homozygous for the added expression cassettes, e.g., a transgenic plant that contains two sets of added expression cassettes, one set at the same locus on each chromosome of a chromosome pair. A homozygous transgenic plant can be obtained by sexually mating (selfing) an independent segregant transgenic plant that contains a single added set of cassettes, germinating some of the seed produced and analyzing the resulting plants produced for enhanced of one or the other expressed genes relative to a control (native, non-transgenic) or an independent segregant transgenic plant. A homozygous transgenic plant can exhibit at least enhanced expression of the selectable marker as compared to both a native, non-transgenic plant and an independent segregant transgenic plant. A homozygous transgenic plant can also be prepared from transformed microspores, as noted before.

It is to be understood that two different transgenic plants can be mated to produce offspring that contain two sets of independently added segregating cassette sets. Selfing of appropriate progeny can produce plants that are homozygous for both added cassette sets. Back-crossing to a parental plant and out-crossing with a non-transgenic plant are also contemplated.

A transgenic plant of this invention thus has heterologous DNA containing two expression cassettes (a set). A preferred transgenic plant is an independent segregant for the added set of cassettes and can transmit those cassettes and their activity to its progeny. A more preferred transgenic plant is homozygous for those heterologous cassette sets, and transmits those genes to all of its offspring on sexual mating.

Where alleic variations among siblings of a cross are small, as with an extensively inbred plant, comparisons between siblings of the same type or same strain can be used or an average arrived at using several siblings. Otherwise, clones are preferred for the comparison.

Plant Transformation Kit

Another aspect of this invention is a kit for transforming plant cells. This kit, which itself is usually contained in a package, contains two packages and also preferably contains a set of directions for use of the kit.

A first package contains a DNA segment heterologous to the plant to be transformed. That DNA segment contains an expression cassette operatively linked to a linker segment that includes at least one restriction endonuclease site, and preferably includes a plurality of such sites. The expression cassette is a first (or third) expression cassette discussed before that contains a heterologous DNA selectable marker segment that includes (i) a first gene that encodes a heterologous enzyme that converts an encrypted carbon source that does not support growth and proliferation of non-transformed plant cells into a carbon source that supports growth and proliferation of the transformed cells upon expression during heterotrophic culture of the transformed plant cells. That gene is operatively linked to (ii) a promoter DNA segment that controls the expression of that heterologous enzyme and (iii) a termination DNA segment.

The first gene can encode any of the before-discussed heterologous enzymes, with the pmi gene being one preferred gene. Another preferred gene is the mannitol 1-oxidoreductase gene that converts mannitol into mannose and is useful for situations where double transformation is contemplated.

The promoter and termination DNA segments are those discussed before in connection with the first expression cassette. A repressible promoter DNA segment is particularly preferred.

The linker segment of this DNA preferably contains a plurality of endonuclease restriction sites as are commonly found in vectors. This linker and its one or more restriction sites facilitates incorporation of a second expression cassette of the user's choice into the heterologous DNA segment. The linker segment can be located upstream or downstream of the first expression cassette.

The DNA of the first package is itself preferably within the TDNA borders of the Ti plasmid of Agrobacterium tumefaciens in a vector adapted for Agrobacterium-mediated plant transformation. Thus, an expression vector is contemplated for Agrobacterium-mediated plant transformation that contains all of the elements needed for that transformation except for the second expression cassette containing the second, target, gene and its promoter and termination segments that are supplied by the user.

Another embodiment of this aspect of the invention includes one or the other or both of 5'-promoter and 3'-termination DNA segments with an operatively-linked linker containing at least one restriction site there between so that all that the user need do is insert (ligate) a desired second, target, gene. These segments can be located together upstream or downstream of the recited expression cassette.

The second package of the kit contains minimal nutrients required for growth and proliferation of non-transformed plant cells during heterotrophic culture, except for a source of carbon. The source of carbon usually present in such nutrient media is replaced by an encrypted carbon source that does not support growth and proliferation of non-transformed plant cells but supports growth and proliferation of transformed plant cells whose genome contains a before-described DNA segment containing a first expression cassette.

A nutrient medium contemplated here as present in the second package can be any useful medium such as any of the media discussed herein like MS medium containing MS salts and RO vitamins that is free of a usual carbon source. The encrypted carbon source is also a previously discussed encrypted carbon source such as mannose, lactose, sorbitol or mannitol as a second encrypted carbon source.

A third package can also be included that contains components of a regeneration medium and the same encrypted carbon source. Thus, nutrient materials such as MS salts and RO vitamins are included along with plant hormones such as benzyladenine and gibberellic acid, and the like as are well known. Antibiotics such as carbenicillin and timentin or ticarcillin that eliminate Agrobacteria can also be included. Each of the ingredients is present in its usually-used amount except for phosphorous that is preferably present at about 1.5 to about 3 times its usual amount in such a medium as a water-soluble phosphate salt.

The packages enclosing the DNA segment and media are those usually used for such purposes. These packages include glass and plastics such as poly(ethylene) and polypropylene), as well as plastic-lined sachets.

Results

The first step in the heterotrophic complementation selection system is to identify a carbon source such as a carbohydrate that is not metabolized by plant cells to support growth and proliferation. Examples of such carbohydrates are mannose, mannitol, sorbitol, lactose, trehalose and salicin.

The second step in the carbon source-based selection system is to select a gene that encodes an enzyme that permits the transformed tissue to utilize that encrypted carbon source, whereas that carbon source is not normally metabolized by non-transformed plant tissue. One particular exemplary gene is that encodes the enzyme phosphomannose isomerase (pmi; EC 5.3.1.8). This enzyme reversibly catalyzes the conversion of fructose 6-phosphate to mannose 6-phosphate. This gene is designated as the pmi gene in *Rhizobium meliloti* (*Gene,* 122: 35–43), *Pseudomonas aeruginosa* (*Gene,* 42:293–302), *Saccharomyces cerevisiae* (*Molecular and Cellular Biology,* 12:2924–2930) and *Salmonella typhimurium* (*Gene,* 103:135–136). In *Escherichia coli*, the phosphomannose isomerase gene is called mana (*Gene,* 32:41–48).

Selection of a Growth-limiting Carbohydrate

All media used herein was that of Murashige and Skoog, *Physiol. Plant,* 15:437–498 (1962) (Medium MS) salts and RO vitamins (composition listed below) that were adjusted to pH=5.7 and solidified with 9 g/L of Noble Agar (Gibco). Medium R1F was MS supplemented with 1 mg/L indoleacetic acid (IAA), 0.65 mg/L zeatine and 16 g/L glucose. Medium MR1 was MS supplemented with 1 mg/L IAA, 0.65 mg/L zeatine and 16 g/L mannose. Medium MR1/2 was MS supplemented with 0.5 mg/L IAA, 0.325 mg/L of zeatine and 16 g/L mannose. Medium RO was MS supplemented with 16 g/L glucose. Medium MRO was MS supplemented with 16 g/L mannose.

TABLE 2

Composition of media used in tomato regeneration.

| | mg/L |
|---|---|
| Medium MS Salts | |
| Ammonium nitrate | 1650.000 |
| Boric acid | 6.200 |
| Calcium chloride | 440.000 |
| Cobaltous chloride | 0.025 |
| Cupric sulfate pentahydrate | 0.025 |
| Ferrous sulfate septahydrate | 27.800 |
| Magnesium sulfate septahydrate | 370.000 |
| Manganese sulfate monohydrate | 15.600 |
| Potassium iodide | 0.083 |
| Potassium nitrate | 1900.000 |
| Potassium phosphate monobasic | 170.000 |
| Sodium ethylenediamine tetraacetate | |
| Sodium molybdate dihydrate | 0.250 |
| Zinc sulfate septahydrate | 8.600 |
| RO Vitamins | |
| Nicotinic acid | 5.000 |
| Thiamine HCl | 0.500 |
| Pyridoxine | 0.500 |
| Myo-inositol | 100.000 |
| Glycine | |

Tomato seeds were sterilized in a solution containing 20 percent of a commercial household bleach containing 5.25 percent sodium hypochlorite for 20 minutes, rinsed 3 times in sterile distilled water and planted on RO medium solidified with 10 g/L of Noble agar (Gibco) in 135 mm Phytacon™ tissue culture vessels (Sigma, St. Louis, Mo.). Seeds were germinated for 72 hours at 25° C. in the dark, then moved to a lighted shelf under approximately 80 $\mu$molm$^{-}$$_2$s$^{-1}$ photosynthetic photon flux density (PPFD), at 24–26° C. Plant tissue used for regeneration was prepared by removing cotyledons from 7-day-old seedlings and cutting them into three parts (proximal, middle and distal to the growing point). The middle and proximal parts were used for the evaluation of growth on potential non-useful carbohydrates.

The following carbohydrates were considered for use as a non-useful encrypted, replacement of a carbon source in plant regeneration medium: mannose, mannitol, sorbitol, lactose, $\alpha,\alpha$-trehalose and salicin. Different R1F media were prepared, each containing one of those carbohydrates added at 0.09 M concentration as a sole carbon source. Control R1F medium contained 0.09M (16 g/L) glucose as a carbon source. Tomato tissue was placed abaxial side down on the media and incubated in sealed petri plates at 24–26° C., under 30 $\mu$molm$^{-2}$s$^{-1}$ PPFD, 16 hours photoperiod. Tomato tissue was observed for signs of regeneration weekly.

Throughout the carbohydrate evaluation, which lasted four weeks, none of the altered media containing the above-listed carbohydrates supported regeneration of tomato shoots, whereas tomato tissue placed on the control glucose-supplemented R1F medium produced abundant shoots.

Selection of a Gene to Convert an Encrypted Carbohydrate

It is known that plants can take mannose up from media, and presumably can subsequently phosphorylate mannose into mannose-6-phosphate. It is concluded that mannose-6-phosphate does not support growth and proliferation of plant cells because plant cells cultured using mannose as the sole carbon source do not grow and proliferate. A gene was therefore chosen that encodes an enzyme that converts mannose-6-phosphate into fructose-6-phosphate. Fructose-6-phosphate is a compound known to be metabolized by plants. Thus, plant cells that express this gene are able to utilize mannose to grow and proliferate, and have a selective growth advantage when placed on media containing mannose as the sole carbon source.

Construction of the Transfer Vector

Figure 2:
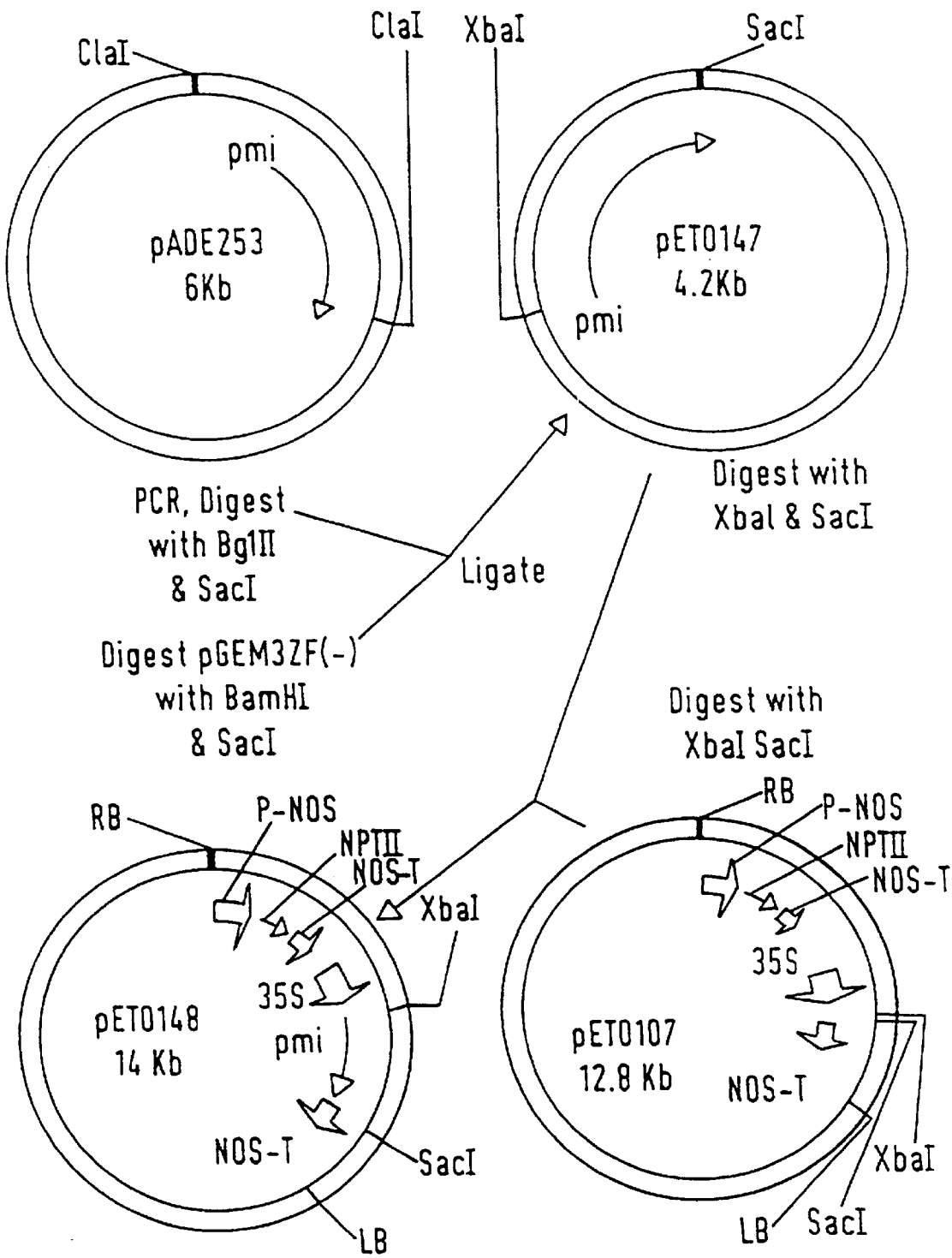
FIG. 2 illustrates the construction of plasmid vector pETO148. The recombinant DNAs manipulated and produced by the construction process are indicated in the figure by the circles. The construction proceeds by a series of steps as indicated by the arrows connecting the circles in the figure and as described in detail herein. Landmark and utilized restriction enzyme recognition sites are indicated on the circles by labeled lines intersecting the circles. The relative location of individual genes and their direction of transcription are indicated by the labeled arrows inside the circles.

A pmi gene from a prokaryotic species was selected and used to create a plant transformation vector that included a selectable marker of the present invention. Molecular biology techniques, that are well known to those skilled in the art, were used to create the plant transformation vector containing the selectable marker gene. The steps used to move the pmi gene into a plant transformation vector are shown in FIG. 2. Enzymes used to manipulate DNA can be purchased either from New England Biolabs or Boehringer Mannheim.

Briefly, plasmid pADE253, containing the S. typhimurium pmi gene (GenBank accession number X57117), was a gift from Dr. James Hackett, University of Adelaide. Plasmid pADE253 is a derivative of the commonly used E. coli cloning vector pBR322 that contains a 1650 base pair (bp) ClaI fragment (FIG. 2) that contains the pmi gene. SEQ ID NO:1 shows the sequence of the 1650 bp ClaI fragment, which contains 432 bases 5' to the beginning of the pmi coding region, 391 codons that contain the coding capacity for the pmi gene product (a protein of predicted Mr of 42.6 kDa), and 43 bases 3' to the TAG stop codon.

SEQ ID NOs:3 and 4 are two oligonucleotides that were prepared to facilitate cloning the pmi gene from pADE253 into a plant transformation vector. The oligonucleotide of SEQ ID NO:3 is 20 bases in length and is identical to bases 391–410 of the ClaI fragment (coding strand), except for position 403 where there is single mismatch. The oligonucleotide of SEQ ID NO:4 is 25 bases in length and is of complimentary sequence to bases 1641–1617 of the ClaI fragment, except for mismatches at positions 1628 and 1630.

The two oligonucleotides and DNA from plasmid pADE253 were used in a polymerase chain reaction (PCR) to amplify a population of approximately 1250 bp DNA fragments containing the pmi coding region and small portions of the upstream and downstream regions. As a result of the mismatched bases between the oligonucleotides and the ClaI fragment and because most of the DNA synthesized in the PCR reaction used newly synthesized DNA as a template rather than the pADE253 DNA as a template, the majority of the approximately 1250 bp fragments synthesized contained two new restriction endonuclease recognition sites that facilitated the cloning of the pmi gene into a plant transformation vector.

The new restriction endonuclease recognition sites added were a BglII recognition site (AGATCT), located between 24 and 29 bases 5' to the initiator methionine codon of the pmi gene, and a SacI recognition site (GAGCTC), located between 21 and 26 bases 3' to the TAG stop codon of the pmi gene. The DNA from the PCR reaction was digested with BglII and SacI for several hours at 37° C., and then electrophoresed on a 1 percent low melting point agarose gel. An approximately 1225 bp band was excised from the gel, and the DNA was isolated and purified.

This fragment, containing the pmi gene, was cloned into the plasmid pGEM3Zf(−) (FIG. 2). Plasmid pGEM3Zf(−) is a commercially available vector (Promega Corporation), and is 3199 bps in length. More specifically, pGEM3Zf(−) DNA was digested with BamHI and SacI, and the vector fragment was gel-purified. Digestion with SacI leaves a four base, 3' overhang of the sequence AGCT. Although the recognition sites for BamHI and BglII are different, both enzymes produce an identical four base, 5' overhang of the sequence GATC. These overhanging regions greatly facilitate directional cloning.

The approximately 1.2 kilobase pair kbp BglII-SacI fragment containing the pmi gene and the BamHI and SacI digested pGEM3Zf(−) DNA were ligated together overnight (about 18 hours) at 16° C. The following day, the ligation reaction product was used to transform E. coli strain MV1190. Various aliquots from the transformation were spread onto LB agar plates supplemented with carbenicillin (100 mg/L), isopropyl-1-thio-β-D-galactoside (IPTG) (0.1 mM), and 5-bromo-4-chloro-3-indolyl-β-D-galactoside (X-gal) (1 ml/L of a 20 mg/mL stock dissolved in N,N dimethylformamide).

Plasmid pGEM3Zf(−), like many commonly used plasmids in molecular biology, has a color marker selection system to indicate when DNA has been inserted into the vector's polylinker. When E. coli containing the omega fragment of β-galactosidase, which is usually contained on the F' plasmid and harboring the pGEM3Zf(−) plasmid are plated onto medium supplemented with IPTG and X-gal, the α-fragment of β-galactosidase, which is encoded by the plasmid, can complement the omega fragment and produce a functional β-galactosidase enzyme. β-galactosidase can cleave the X-gal in the medium, yielding a blue color. Normally, when DNA is inserted into the polylinker region of pGEM3Zf(−), α-complementation is destroyed, and the colonies appear white instead of blue.

The day following transformation, plasmid DNA was purified from several of the white colonies that grew on the LB-carbenicillin-IPTG-X-gal plates. To confirm the presence of the pmi gene, these plasmid DNAs were examined by their gel electrophoresis profiles after digestion with various restriction endonuclease enzymes. A clone that contained the pmi gene was selected from this population and the plasmid was designated as pETO147 (FIG. 2).

The pmi gene was excised from plasmid pETO147 and inserted into a binary vector that facilitated transformation. pETO107 is approximately 13 kbp in length, and is a derivative of the commonly used binary plant transformation vector BIN19 [Bevan, Nucleic Acids Res., 12: 8711–8721 (1984)]. Like BIN19, plasmid pETO107 has both a right and left TDNA border region. These 25 base pair TDNA regions specify the sites that are recognized by Agrobacterium tumefaciens, which mediates the transfer of DNA from the plasmid to the plant chromosome; DNA between these borders is inserted into the plant chromosome by A. tumefaciens. Infecting a number of different plant tissue types, such as leaf discs or cotyledons with A. tumefaciens that harbor a binary vector is a preferred method of transforming many plant species. Outside the TDNA borders, plasmid pETO107 contains the bacterial nptIII gene, which can confer kanamycin resistance to E. coli that harbor this plasmid.

Plasmid pETO107 has two expression cassettes of interest between the TDNA borders. Starting from the right TDNA border and proceeding clockwise for convenience (FIG. 2), the first cassette is composed of three elements that are operationally linked. The first element is the nopaline synthase promoter (P-Nos), which when inserted into the plant chromosome directs the constitutive expression in most plant cells of genes that are positioned downstream of this DNA (clockwise in FIG. 2). The next element is the coding region for the neomycin phosphotransferase type II gene (NPTII). If NPTII is expressed in most plant cells in sufficient quantities, it confers resistance to those cells to the antibiotic kanamycin. The third and final element of the first cassette is the 3' termination end of the nopaline synthase coding region (Nos-T), which contains the polyadenylation recognition site. The first cassette is commonly used in plant transformation vectors as a selectable marker to identify transformed tissue; the kanamycin resistance conferred to transformed cells results in a selective growth advantage on medium supplemented with kanamycin. The nptII expression cassette is part of the original plasmid, and is not essential for the current invention, but is rather an example of a before-discussed second expression cassette.

Proceeding clockwise in FIG. 2, the second expression cassette in plasmid pETO107 also contains three elements. The first element is the 35S promoter (35S) from cauliflower mosaic virus (CaMV 35S). Like the P-Nos promoter, CaMV 35S directs constitutive expression in plant cells. Generally, the level of expression in plant cells is greater with CaMV 35S than P-Nos. The next element is a polylinker and includes the recognition sites for the following restriction endonuclease enzymes: XbaI, BamHI, SmaI, KpnI and SacI. The third and final element of this cassette is the 3' termination end of the nopaline synthase coding region (Nos-T). The polylinker region of this second element was used to insert the XbaI-SacI fragment from pETO147, which contains the pmi gene, into the XbaI and SacI sites that are located between the CaMV 35S and Nos-T elements.

DNA from plasmids pETO147 and pETO107 were digested with XbaI and SacI. The approximately 1.2 kbp XbaI-SacI fragment from plasmid pETO147, and the 13 kbp XbaI-SacI fragment from plasmid pETO107 were gel-purified. In a ligation reaction containing the 1.2 kbp XbaI-SacI fragment from plasmid pETO147 containing the pmi gene, and the 13 kbp XbaI and SacI plasmid pETO107 fragment, the 4-base overhangs facilitated the directional insertion of the pmi gene between the CaMV 35S promoter and Nos-T. The ligation reaction was performed overnight (about 18 hours) at 16° C.

The following day, the ligation reaction product was used to transform the E. coli strain XL1-Blue MRF'. Various aliquots from the transformation were spread onto LB agar plates supplemented with kanamycin (50 mg/L). The following day, plasmid DNA was purified from several colonies, and gel electrophoresis profiles from restriction endonuclease digestions were used to identify a plasmid containing a pmi gene that was inserted between the CaMV 35S and Nos-T elements. One such plasmid was designated pETO148 (FIG. 2).

Plasmid pETO148 was deposited at the American Type Culture Collection, 12301 Parklawn Drive, Rockville, Md. on Apr. 6, 1995 and was given ATCC accession number 97107. The present deposit was made in compliance with the Budapest Treaty requirements that the duration of the deposit should be for 30 years from the date of deposit or for five years after the last request for the deposit at the depository or for the enforceable life of a U.S. patent that matures from this application, whichever is longer. The vector will be replenished should it become non-viable at the depository.

E. coli harboring plasmid pETO148 were mobilized into the disarmed A. tumefaciens strain LBA4404 using the triparental mating system to form *A. tumefaciens* pETO148::LBA4404. Transconjugants were used to transform tomato (*Lycopersicon esculentum*).

To examine the dynamics of transformation and regeneration on mannose in several crops, a scorable marker was added to the plasmid pETO148 transformation vector. Specifically, an additional expression cassette, containing the CaMV 35S promoter, β-glucuronidase coding region and Nos-T was inserted into plasmid pETO148. The resultant vector, designated plasmid pETO156, was mated into *A. tumefaciens* by the triparental method.

EXAMPLE 1

Transformation of Tomato Plants

Tomato seeds were sterilized in a solution containing 20 percent of a commercial household bleach containing 5.25 percent sodium hypochlorite, rinsed three times in sterile distilled water and planted on Murashige and Skoog (MS) medium (Gibco) solidified with 10 grams of Noble agar (Gibco) in 135 mm Phytacon™ tissue culture vessels (Sigma, St. Louis, Mo.). Seeds were germinated for 72 hours at 25° C. in the dark, then moved to a lighted shelf under approximately 80 $\mu molm^{-2}s^{-1}$ PPFD, at 24–26° C. Plant tissue used for transformation was prepared by removing cotyledons from 7-day-old seedlings and cutting them into three parts (proximal, middle and distal to the growing point).

The middle and proximal parts were used for co-cultivation with Agrobacterium. Those parts were placed abaxial side down on a sterile filter paper overlaying co-cultivation medium R1F supplemented with 0.09 M (16 g/L) glucose, and incubated in the dark for 24 hours. Next, they were incubated for 20 minutes with bacterial inoculum containing $5 \times 10^8$ CFU/mL of *Agrobacterium tumefaciens*, pETO148::LBA4404, blotted dry, and cultured for 48 hours, at 24° C., in the dark.

Bacterial inoculum was prepared by growing *A. tumefaciens*, pETO148::LBA4404, in 25 ml of AB medium [Chilton et al., 1974, *Proc. Natl. Acad. Sci. USA*, 71:3672–3676 (1974)] supplemented with 50 mg/L kanamycin (K) and 25 mg/L streptomycin (St) ($AB_{K50St25}$) on a shaker at 28° C., 180 rpm, for 24 hours. One mL of this culture was transferred to 25 mL of fresh $AB_{K50St25}$ medium and grown on a shaker at 28° C., 180 rpm for 24 hours. The bacteria were then pelleted by centrifuging at 8000 rpm for 10 minutes in a Beckman J2-21 centrifuge using a JA-20 rotor. The bacterial pellet was resuspended in sterile MS medium and their concentration was adjusted to $5 \times 10^8$ CFU/mL using spectrophotometric optical density reading at 550 nm (0.1 $OD_{550}$ $2 \times 10^8$ CFU/mL). Prior to co-cultivation, the inoculum was supplemented with acetosyringone (3',5'-dimethoxy-4'hydroxy-acetophenone, Sigma, St. Louis, Mo.) to a final concentration of 600 $\mu M$.

Selection of Transformed Tomato Plants

After the 48 hour co-cultivation period with the Agrobacterium (pETO148::LBA4404) on the R1F medium, tomato tissue was moved to MR1 regeneration medium containing 0.09 M mannose as the sole carbon source. The MR1 medium was supplemented with 100 mg/L of the antibiotic ticarcillin (Duchefa Co.) to eliminate Agrobacterium. After two weeks of culture, tomato tissue was moved to fresh MR1 medium. At this time small calli were visible on the cut ends of co-cultivated tissue, whereas control tissue that was not co-cultivated with the bacteria but was also cultured on the MR1 medium, showed yellowing and did not produce any callus. After two more weeks of culture all tissues were moved to MR1/2 regeneration medium also containing 0.09 M mannose as a sole carbon source. At this time the co-cultivated tissue produced a thick ridge of callus with small shoot primordia, whereas the control tissue was yellow in color, did not enlarge, nor produce callus. After two weeks on the MR1/2 medium the calli and shoot primordia that formed on the co-cultivated tissue were detached from the original tissue and moved to MRO medium supplemented with 0.09M mannose. On this medium the shoots elongated and developed roots. Rooted plants were potted and moved to the greenhouse.

Biochemical and Molecular Analysis of Regenerated Plants

Plants regenerated on mannose were assayed biochemically and molecularly to determine whether they were transformed. These plants were selected by their ability to grow on a medium containing mannose as an encrypted carbon source, but because the pETO148 transformation vector contained both the pmi and the nptII genes, they were assayed for transformation indirectly by scoring for the expression of the second gene (nptII) using a commercially available (5 Prime→3 Prime, Inc.) NPTII enzyme linked immunoabsorbant assay (ELISA).

FIG. 3 shows the relative NPTII expression from three rank-ordered populations. One population included five tomato plants that were non-transformed (negative control). The second population of five plants was from a transformation study that used kanamycin as a selective agent. In these positive control plants, the NPTII ELISA assays directly for the expression of the selective marker gene which detoxifies the selective agent. The expression of NPTII in these plants covered a wide range. The third population were 16 plants selected on mannose. The NPTII expression in the plants selected on mannose also covered a wide range. The expression of NPTII in the plants selected on mannose indicated that the nptII expression cassette that is incorporated with the pmi expression cassette was functioning in plants, and supplied indirect evidence that these plants were transformed. Further, these data indicate that the expression from the pmi gene, which confers the ability to grow on mannose, did not affect expression of an adjacent gene in the plant's chromosome.

To assay directly for transformation, a Southern blot was performed on several putative transformants. A Southern blot is a commonly performed assay in molecular biology that can show how many copies of the transgene of interest are incorporated into the genome. Five grams of young leaf tissue were harvested and used to isolate genomic DNA. DNA yields were quantitated using a Hoefer Model TKO100 Fluorometer.

For each sample, 10 $\mu g$ of DNA was digested with HindIII, electrophoresed on a 1 percent agarose gel and transferred to a nylon membrane. DNAs were fixed to the membrane using a Stratagene CL-100 ultraviolet crosslinker. The Genius™ non-radioactive detection system (Boehringer Mannheim) was used to probe the membrane and the blot results were recorded by fluorography. Using primers specific for the pmi gene, a 788 bp fragment was amplified using PCR. During amplification, digoxigenin-11-dUTP was incorporated into the PCR fragments. The pmi-specific, digoxigen-labeled fragments were used to probe the genomic blot. Protocols for the hybridization, blot washing and visualization were supplied by the manufacturer.

A fluorogram of 11 putative transgenic samples was prepared using molecular mass markers from HindIII-digested bacteriophage lambda DNA and DNA from a non-transformed tomato plant as a negative control. The blot showed that the pmi probe did not hybridize to the DNA from the non-transformed parental control, but did decorate specific bands in nine of the eleven putative transformants. The number of copies inserted into the tomato genome varied.

EXAMPLE 2

Monocot Cell Growth on Mannose

To assay whether mannose could be used for selection of transgenic cells in monocot plants the growth of cell suspensions of both oats and corn (maize) was evaluated in sucrose-supplemented media (standard protocol) and in media in which sucrose was replaced with mannose at the same molar concentration.

Oats

Approximately 500 mg of drained oat suspension cells were inoculated to 40 ml of liquid MS2-D medium (4.4 g/L MS salts, Sigma #M5524; 0.5 mg/L thiamine HCl; 2 mg/L 2,4-D; 150 mg/L L-asparagine; pH=5.8) containing either 0.06 M sucrose (20 g/L) or 0.06 M mannose (10.6 g/L). Each treatment was replicated three times. The flasks were placed on a shaker at 160 rpm, 24–26° C., using 16 hours of photoperiod. After 25 days, the suspension cells were allowed to settle at the bottom of a test tube, the liquid medium was aspirated and the cells were weighed. The net weights of the cells are listed in Table 3, below.

TABLE 3

Net weight (grams) of Oat Suspension Cells After Culture in Media Supplemented Either with Sucrose or Mannose as Carbon Source

| Replicate | Sucrose | Mannose |
| --- | --- | --- |
| 1 | 3.03 | 0.79 |
| 2 | 3.33 | 0.66 |
| 3 | 3.41 | 0.92 |
| Mean ± SE | 3.26 ± 0.12 | 0.79 ± 0.08 |

Corn (Maize)

A rapidly growing suspension culture of black Mexican sweet corn (BMS) was washed several times in mannose-supplemented (10.6 g/L) MS-F medium (4.4 g/L MS salts, Sigma #M5524; 1.3 mg/L nicotinic acid; 0.25 mg/L pyridoxine HCl; 0.25 mg/L thiamine HCl; 0.25 mg/L calcium pantothenate; 2 mg/L 2,4-D; 0.1 g/L inositol; 150 mg/L L-asparagine; pH=5.8). A five mL aliquots of a thick (1:1 cells to liquid ratio) cell slurry made from the washed cells were inoculated to flasks containing 35 mL of either mannose-supplemented (0.06 M) or sucrose-supplemented (0.06 M) medium. Each treatment was replicated four times. The flasks were placed on a shaker at 160 rpm, 24–26° C., in the dark. The growth of the suspension cells was assessed after 32 days of culture by measuring the packed cell volume. The results are presented in Table 4, below.

TABLE 4

Volume (cc) of Corn Suspension Cells After Culture in Media Supplemented Either with Sucrose or Mannose

| Replicate | Sucrose | Mannose |
| --- | --- | --- |
| 1 | 8.4 | 1.8 |
| 2 | 7.6 | 2.0 |
| 3 | 8.0 | 2.4 |
| 4 | 10.4 | 2.0 |
| Mean ± SE | 8.60 ± 0.62 | 2.05 ± 0.13 |

Both oat and corn cell suspensions showed severe inhibition of growth when cultured in mannose-supplemented medium as compared to the standard sucrose-containing medium. This indicates that a replacement of sucrose with mannose provides an effective selection for genetically engineered cells from monocot plants that can utilize mannose as a carbon source under heterotrophic growth conditions.

EXAMPLE 3

Regeneration of Transgenic Tomatoes

Tomato tissue was prepared and cocultivated with Agrobacterium containing the pmi gene as described in Example 1. After cocultivation tomato tissue was cultured on the MR media supplemented with 170 mg/L of monobasic potassium phosphate (MR/P media). The supplementation of the mannose-containing media with additional phosphorus resulted in a significant increase in the number of transformed plants that were regenerated. The comparison of regeneration on MR media and MR/P media is shown in Table 5.

TABLE 5

Comparison of Regeneration of Transformed Plants on MR and MR/P Media

| Medium | Frequency of regeneration (Percent) | Number of regenerated shoots | Percent normal shoots | Percent abnormal shoots |
| --- | --- | --- | --- | --- |
| MR | 66.4 | 83 | 48.2 | 51.8 |
| MR/P | 82.4 | 103 | 80.6 | 19.4 |

These observations indicate that an additional modification of the basic medium composition results in increased regeneration of transformed plants. Doubling of the concentration of phosphorus, which is an essential component of the regeneration medium, gave further growth advantage to tomato cells containing the pmi gene, resulting in a more efficient regeneration of genetically engineered plants using mannose for selection.

EXAMPLE 4

Transgenic Melon

Decoated melon seeds were surface sterilized in a solution containing 10 percent of a commercial household bleach containing 5.25 percent sodium hypochlorite for ten minutes, rinsed six times in sterile, distilled water and germinated on a blotter paper soaked with sterile water for 24 hours, in the dark. After germination, cotyledons were detached from the seed axis and cultured on B0 medium for two days under 20 $\mu$mol $m^{-2}s^{-1}$ PPFD. Targeted for transformation tissue was cut out using a No. 1 corkborer and inoculated with Agrobacterium tumefaciens pETO156::EHA by first briefly vortexing and then by soaking the tissue in the bacterial inoculum for 20 minutes.

Inoculated tissue was cultured for three days on a fresh B0 medium overlayed with a sterile filter paper. Cocultivated explants were washed three times in a liquid B0 medium containing 1000 mg/L of the antibiotic carbenicillin and 200 mg/L of the antibiotic timentin to eliminate the Agrobacterium, followed by two weeks of culture on shoot induction medium B300 supplemented with 16 gm/L of mannose, at 24–26° C., under 60–80 $\mu$mol $m^{-2}s^{-1}$ PPFD of light, at 16 hours of photoperiod.

After two weeks on the B300 medium melon tissue was transferred to shoot elongation medium E500 also containing 16 gm/L mannose, and cultured for another two weeks. At the time of transfer to the E500 medium the cocultivated tissue showed rapid cell proliferation, whereas non-transformed control tissue did not enlarge and did not produce any callus. Shoots that developed on the cocultivated tissue were rooted on medium N500 containing 16 gm/L mannose. Noncocultivated control tissue never produced any shoots. Rooted plants were potted. Effective selection of transformed melon plants was confirmed by staining plant tissue in the chemical reagent X-Gluc, which causes the transgenic tissue to turn blue due to the production of indigo dye by transgenic cells.

All media used in melon regeneration contained 4.3 gm/L of MS salts (Gibco #11117-074) and 1 ml/L of MS vitamins (Sigma #7150), were solidified with 8.0 gm/L of Noble agar and had pH adjusted to 5.8. Media B300, E500 and N500 contained 1000 mg/L carbenicillin and 200 mg/L timentin to eliminate the Agrobacterium. The B0 medium used for preculture and cocultivation was supplemented with 30 gm/L of sucrose, whereas media B300, E500 and N500 contained 16 gm/L mannose as a sole carbon source. Medium B300 contained 1.0 mg/l benzyladenine; medium E500 contained 0.15 mg/L benzyladenine and 3 mg/L gibberellic acid; medium N500 contained 50 mg/L 1-naphthylacetic acid and 16 mg/L thiamine Hcl.

A preferred way to regenerate transgenic melon plants using mannose as a selective agent is to use B300, E500 and N500 media supplemented with additional 170 mg/L or 340 mg/L monobasic potassium phosphate.

EXAMPLE 5

Transgenic Squash

Decoated squash seeds were surface sterilized in a solution containing ten percent of a commercial household bleach containing 5.25 percent sodium hypochlorite for ten minutes, rinsed five times in sterile, distilled water and germinated for 24 hours in the dark at 27° C. on filter paper soaked with sterile water. Plant tissue used for transformation was prepared by removing the shoot axis cotyledonary node tissue and the distal half of the cotyledonary tissue. The remaining proximal half was cut into 4 explant pieces.

All explants were inoculated for 10 minutes in $2.5 \times 10^8$ CFU/mL of Agrobacterium tumefaciens, pETO 156:EHA 105 in liquid MS medium supplemented with 0.2 mM acetosyringone. Explants were blotted on sterile filter paper and cocultivated adaxial side down on MS medium supplemented with 2 mg/L 2,4,5-T and 0.5 mg/L kinetin. Explants were cocultivated for 3 days in the dark in unsealed Petri dishes.

After the 3 day cocultivation period, explants were washed for 3 hours in MS liquid medium supplemented 10 mg/L 2,4-D, 0.5 mg/L kinetin, 400 mg/l cefotaxime and 750 mg/L carbenicillin. The rinse medium was changed 3 times during the procedure. Explants were blotted on sterile filter paper and cultured abaxial side down on selection medium consisting of MS salts and vitamins, 10 mg/L 2,4-D, 0.5 mg/L kinetin, 16.2 g/L mannose, 1000 mg/L carbenicikkin and 170 mg/L monobasic potassium phosphate. Explants were cultured in unsealed Petri dishes and kept in diffused light. Explants were subcultured to fresh medium every two weeks.

After 8 weeks of selection, clusters of embryos formed on the edges of the explants cultured on mannose, whereas control explants did not produce any embryos. The transgenic character of the regenerating embryos was confirmed by staining in the chemical reagent X-Gluc, which causes transgenic tissue to turn blue from embryos was achieved by subculture to hormone-free medium for rooting and further development. The transgenic character of the plants regenerated on mannose-containing medium was confirmed by staining in X-Gluc.

The foregoing is intended as illustrative of the present invention but not limiting. Numerous variations and modifications can be effected without departing from the true spirit and scope of the novel concepts of the invention.

---

We claim:

1. A process for selectively growing transformed plant cells in a mixture of transformed and non-transformed plant cells comprising the steps of:
(a) culturing a mixture of transformed and non-transformed plant cells under heterotrophic culture conditions in a culture medium that contains minimal nutrients required for proliferation and growth by non-transformed plant cells except for a source of carbon that supports growth and proliferation and at least about 58.1 mg/L of phosphorus in the culture medium, said source of carbon being replaced by mannose that does not support growth and proliferation of said non-transformed cells, said transformed cells containing a genomic heterologous DNA segment that contains two expression cassettes,
the first expression cassette containing a heterologous DNA selectable marker segment that includes (i) a first gene that encodes phosphomannose isomerase that on expression allows mannose to be converted into a carbon source that supports growth and proliferation of said transformed plant cells under heterotrophic culture conditions, said first gene being operatively linked to (ii) a first promoter DNA segment that controls expression of the phosphomannose isomerase, and (iii) a termination DNA segment;
the second expression cassette containing (i) a second gene that is expressed in a transformed plant and that is operatively linked to (ii) a second promoter DNA segment that controls expression of said second gene and (iii) a termination DNA segment; and
(b) maintaining said heterotrophic culture conditions for a time period sufficient for said transformed plant cells to express the phosphomannose isomerase, to grow and proliferate.

2. The process according to claim 1 wherein said heterologous enzyme is phosphomannose isomerase and said encrypted carbon source is mannose.

3. The process according to claim 1 including the further step of recovering said proliferating cells.

4. The process according to claim 3 including the further step of forming plant meristematic tissues or plant embryos from said proliferating cells.

5. The process according to claim 4 wherein expression from said first promoter DNA sequence is repressed by a product of the normal metabolism of said transgenic plants under autotrophic growth.

6. The process according to claim 5 wherein the repressible first promoter DNA sequence is that of the cucumber malate synthase promoter.

7. The process according to claim 5 wherein the repressible first promoter DNA sequence is that of the cucumber isocitrate lyase promoter.

8. The process according to claim 5 wherein the repressible first promoter DNA sequence is that of the rice α-amylase Amy3A promoter.

9. A process for selectively growing transformed plants from a mixture of transformed and non-transformed plant cells comprising the steps of
(a) culturing a mixture of transformed and non-transformed plant cells under heterotrophic culture conditions in a culture medium that contains minimal nutrients required for proliferation and growth by non-transformed plant cells except for a source of carbon that supports growth and proliferation and at least about 58.1 mg/L of phosphorus in the culture medium, said source of carbon being replaced by mannose that does not support growth and proliferation of said non-transformed cells, said transformed cells containing a genomic heterologous DNA segment that contains two expression cassettes,
the first expression cassette containing a heterologous DNA selectable marker segment that includes (i) a first gene that encodes phosphomannose isomerase that on expression allows mannose to be converted into a carbon source that supports growth and proliferation of said transformed plant cells under heterotrophic culture conditions, said first gene being operatively linked to (ii) a first promoter DNA segment that controls expression of said heterologous enzyme, and (iii) a termination DNA segment,
the second expression cassette containing (i) a second gene that is expressed in a transformed plant and that is operatively linked to (ii) a second promoter DNA segment that controls expression of said second gene and (iii) a termination DNA segment;
(b) maintaining said heterotrophic culture conditions for a time period sufficient for said transformed plant cells to express the phosphomannose isomerase, grow and proliferate;
(c) recovering said proliferating cells; and
(d) forming plant meristematic tissues or plant embryos from said proliferating cells.

10. The process according to claim 9 wherein said heterologous enzyme is phosphomannose isomerase and said encrypted carbon source is mannose.

11. The process according to claim 9 wherein expression from said first promoter DNA sequence is repressed by a product of the normal metabolism of said transgenic plants under autotrophic growth.

12. The process according to claim 11 wherein the repressible first promoter DNA sequence is that of the cucumber malate synthase promoter.

13. The process according to claim 11 wherein the repressible first promoter DNA sequence is that of the cucumber isocitrate lyase promoter.

14. The process according to claim 11 wherein the repressible first promoter DNA sequence is that of the rice α-amylase Amy3A promoter.

15. A process for selectively growing twice-transformed plant cells in a mixture of twice- and once-transformed plant cells comprising the steps of:
(a) culturing a mixture of twice- and once-transformed plant cells under heterotrophic culture conditions in a culture medium that contains minimal nutrients required for proliferation and growth by said once-transformed plant cells except for a source of carbon that supports growth and proliferation of said once-transformed cells and at least about 58.1 mg/L of phosphorus in the culture medium, said source of carbon being replaced by mannitol that does not support growth and proliferation of said once-transformed plant cells; said twice-transformed cells containing first and second heterologous DNA segments that contain four expression cassettes, wherein the first and second expression cassettes are in the first heterologous DNA segment and the third and fourth expression cassettes are in the second heterologous DNA segment;
the first expression cassette containing a heterologous DNA selectable marker segment that includes (i) a first gene that encodes phosphomannose isomerase that on expression allows mannose to be converted into a carbon source that supports growth and proliferation of said once- and twice-transformed plant cells under heterotrophic culture conditions but does not support growth and proliferation of non-transformed plant cells, said first gene being operatively linked to (ii) a first promoter DNA segment that controls expression of the phosphomannose isomerase, and (iii) a termination DNA segment, the second expression cassette containing (i) a second gene that is expressed in a transformed plant and that is operatively linked to (ii) a second promoter DNA segment that controls expression of said second gene and (iii) a termination DNA segment;

the third expression cassette containing a second heterologous DNA selectable marker segment that includes (i) a second gene that encodes mannitol 1-oxidoreductase that on expression during heterotrophic culture of said twice-transformed cells, converts the mannitol that does not support growth and proliferation of once-transformed and non-transformed cells, of the same type into mannose that supports growth and proliferation of said twice-and once-transformed cells, said second gene being operatively linked to (ii) a third promoter DNA segment that controls expression of said second heterologous enzyme, and (iii) a termination DNA segment;

the fourth expression cassette containing (i) a fourth gene that is expressed in said transformed plant and that is operatively linked to (ii) a fourth promoter that controls expression of said forth gene and (iii) a termination DNA segment; and (b) maintaining said heterotrophic culture conditions for a time period sufficient for said twice-transformed plant cells to express said first and second heterologous enzymes, grow and proliferate.

16. The process according to claim 15 wherein said second heterologous DNA selectable marker segment encodes the enzyme mannitol-1-oxo reductase, said second encrypted carbon source is mannitol, said first gene that encodes a heterologous enzyme encodes phosphomannose isomerase and said first encrypted carbon source is mannose.

17. A process for selectively growing transformed plant cells in a mixture of transformed and non-transformed plant cells comprising the steps of:

(a) culturing a mixture of transformed and non-transformed plant cells under heterotrophic culture conditions in a culture medium that contains minimal nutrients required for proliferation and growth by non-transformed plant cells except for a source of carbon that supports growth and proliferation and at least about 178.5 mg/L of phosphate in the culture medium, said source of carbon being replaced by mannose that does not support growth and proliferation of said non-transformed cells, said transformed cells containing a genomic heterologous DNA segment that contains two expression cassettes, the first expression cassette containing a heterologous DNA selectable marker segment that includes (i) a first gene that encodes phosphomannose isomerase that on expression allows mannose to be converted into a carbon source that supports growth and proliferation of said transformed plant cells under heterotrophic culture conditions, said first gene being operatively linked to (ii) a first promoter DNA segment that controls expression of the phosphomannose isomerase, and (iii) a termination DNA segment;

the second expression cassette containing (i) a second gene that is expressed in a transformed plant and that is operatively linked to (ii) a second promoter DNA segment that controls expression of said second gene and (iii) a termination DNA segment; and (b) maintaining said heterotrophic culture conditions for a time period sufficient for said transformed plant cells to express the phosphomannose isomerase, to grow and proliferate.

18. A process for selectively growing transformed plants from a mixture of transformed and non-transformed plant cells comprising the steps of (a) culturing a mixture of transformed and non-transformed plant cells under heterotrophic culture conditions in a culture medium that contains minimal nutrients required for proliferation and growth by non-transformed plant cells except for a source of carbon that supports growth and proliferation and at least about 178.5 mg/L of phosphate in the culture medium, said source of carbon being replaced by mannose that does not support growth and proliferation of said non-transformed cells, said transformed cells containing a genomic heterologous DNA segment that contains two expression cassettes, the first expression cassette containing a heterologous DNA selectable marker segment that includes (i) a first gene that encodes phosphomannose isomerase that on expression allows mannose to be converted into a carbon source that supports growth and proliferation of said transformed plant cells under heterotrophic culture conditions, said first gene being operatively linked to (ii) a first promoter DNA segment that controls expression of said heterologous enzyme, and (iii) a termination DNA segment, the second expression cassette containing (i) a second gene that is expressed in a transformed plant and that is operatively linked to (ii) a second promoter DNA segment that controls expression of said second gene and (iii) a termination DNA segment;

(b) maintaining said heterotrophic culture conditions for a time period sufficient for said transformed plant cells to express the phosphomannose isomerase, grow and proliferate;

(c) recovering said proliferating cells; and (d) forming plant meristematic tissues or plant embryos from said proliferating cells.

19. A process for selectively growing twice-transformed plant cells in a mixture of twice- and once-transformed plant cells comprising the steps of:

(a) culturing a mixture of twice- and once-transformed plant cells under heterotrophic culture conditions in a culture medium that contains minimal nutrients required for proliferation and growth by said once-transformed plant cells except for a source of carbon that supports growth and proliferation of said once-transformed cells and at least about 178.5 mg/L of phosphate in the culture medium, said source of carbon being replaced by mannitol that does not support growth and proliferation of said once-transformed plant cells; said twice-transformed cells containing first and second heterologous DNA segments that contain four expression cassettes, wherein the first and second expression cassettes are in the first heterologous DNA segment and the third and fourth expression cassettes are in the second heterologous DNA segment;

the first expression cassette containing a heterologous DNA selectable marker segment that includes (i) a first gene that encodes phosphomannose isomerase that on expression allows mannose to be converted into a carbon source that supports growth and proliferation of said once-transformed plant cells under heterotrophic culture conditions but does not support growth and proliferation of non-transformed plant cells, said first gene being operatively linked to (ii) a first promoter DNA segment that controls expression of the phosphomannose isomerase, and (iii) a termination DNA segment, the second expression cassette containing (i) a second gene that is expressed in a transformed plant and that is operatively linked to (ii) a second promoter DNA segment that controls expression of said second gene and (iii) a termination DNA segment;

the third expression cassette containing a second heterologous DNA selectable marker segment that includes (i) a second gene that encodes mannitol 1-oxidoreductase that on expression during heterotrophic culture of said twice-transformed cells converts the mannitol that does not support growth and proliferation of once-transformed and non-transformed cells, of the same type into mannose that supports growth and proliferation of said twice- and once-transformed cells, said second gene being operatively linked to (ii) a third promoter DNA segment that controls expression of said second heterologous enzyme, and (iii) a termination DNA segment;

the fourth expression cassette containing (i) a fourth gene that is expressed in said transformed plant and that is operatively linked to (ii) a fourth promoter that controls expression of said fourth gene and (iii) a termination DNA segment; and (b) maintaining said heterotrophic culture conditions for a time period sufficient for said twice-transformed plant cells to express said first and second heterologous enzymes, grow and proliferate.

* * * * *